(12) United States Patent
Rao et al.

(10) Patent No.: US 12,312,301 B2
(45) Date of Patent: May 27, 2025

(54) ORGANOSULFUR COMPOUNDS

(71) Applicant: MARIPOSA THERAPEUTICS LTD., Abertillery Gwent (GB)

(72) Inventors: Kodanda Ranganatha Nagraja Rao, Abertillery (GB); Christopher Gregory Newton, Abertillery (GB); Gareth James Street Evans, Abertillery (GB)

(73) Assignee: MARIPOSA THERAPEUTICS LTD., Abertillery Gwent (GB)

( * ) Notice: Subject to any disclaimer, the term of this patent is extended or adjusted under 35 U.S.C. 154(b) by 534 days.

(21) Appl. No.: 17/290,355

(22) PCT Filed: Nov. 4, 2019

(86) PCT No.: PCT/GB2019/053116
§ 371 (c)(1),
(2) Date: Apr. 30, 2021

(87) PCT Pub. No.: WO2020/095031
PCT Pub. Date: May 14, 2020

(65) Prior Publication Data
US 2022/0009882 A1 Jan. 13, 2022

(30) Foreign Application Priority Data

Nov. 5, 2018 (GB) ..................................... 1818029

(51) Int. Cl.
*C07C 323/65* (2006.01)
*A61K 31/10* (2006.01)

(52) U.S. Cl.
CPC ........ *C07C 323/65* (2013.01); *C07C 2601/16* (2017.05)

(58) Field of Classification Search
CPC .............................. C07C 323/65; A61K 31/10
See application file for complete search history.

(56) References Cited

U.S. PATENT DOCUMENTS 4,643,994 A 2/1987 Block et al.

FOREIGN PATENT DOCUMENTS

KR 10-2018-000942 A 1/2018

OTHER PUBLICATIONS

EPO (Riswijk, NL), English language version of the International Search Report, Form PCT/ISA/210, for International Application PCT/GB2019/053116, Jan. 29, 2020 (2 pages).

*Primary Examiner* — Sikarl A Witherspoon
(74) *Attorney, Agent, or Firm* — Pauley Erickson & Swanson

(57) ABSTRACT

Organosulfur compounds of Formula (I), and pharmaceutical compositions comprising these organosulfur compounds. Methods of using the organosulfur compounds and the pharmaceutical compositions for treating infection, and/or for treating inflammation, and/or for reducing the formation of blood clots.

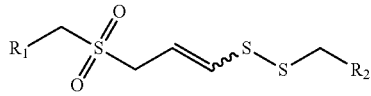

Formula (I)

20 Claims, 3 Drawing Sheets

ORGANOSULFUR COMPOUNDS

CROSS REFERENCE TO RELATED APPLICATION

This application is a National Phase filing of PCT International Patent Application PCT/GB2019/053116, filed on 4 Nov. 2019. The co-pending parent application is hereby incorporated by reference herein in its entirety and is made a part hereof, including but not limited to those portions which specifically appear hereinafter.

TECHNICAL FIELD

The present invention generally relates to organosulfur compounds of formula (I) and pharmaceutical compositions comprising one or more organosulfur compounds of formula (I). The present invention also relates to methods of making the organosulfur compounds of formula (I). The present invention further relates to the various uses of the organosulfur compounds of formula (I), for example as an antimicrobial agent, as an anti-inflammatory agent, as an anti-thrombotic agent, for the treatment of a wound and/or for the treatment of cystic fibrosis and/or for the treatment of epidermolysis bullosa.

BACKGROUND

A number of organosulfur compounds are known to have physiological effects. For example, ajoene, an organosulfur compound found in garlic extract, is known to have antimicrobial, anti-inflammatory, and anti-thrombotic effects. It is therefore desirable to obtain new alternative or improved organosulfur compounds that may have one or more advantageous physiological effects.

SUMMARY

In accordance with a first aspect of the present invention there is provided a compound of formula (I)

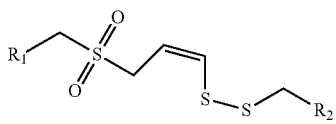

Formula (I)

wherein $R_1$ is phenyl, substituted phenyl, cycloalkyl, substituted cycloalkyl, heterocyclyl, or substituted heterocyclyl; and $R_2$ is phenyl, substituted phenyl, cycloalkyl, substituted cycloalkyl, or alkenyl.

The compound of formula (I) may have E or Z configuration. Thus, in certain embodiments the compound may be according to formula (IA) or formula (IB)

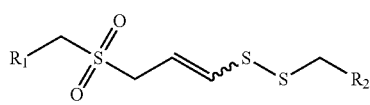

Formula (IA)

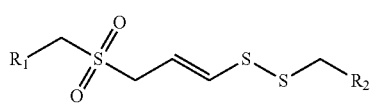

Formula (IB)

wherein $R_1$ is phenyl, substituted phenyl, cycloalkyl, substituted cycloalkyl, heterocyclyl, or substituted heterocyclyl; and $R_2$ is phenyl, substituted phenyl, cycloalkyl, substituted cycloalkyl, or alkenyl.

There is also provided herein a composition comprising a mixture of an E stereoisomer and a Z stereoisomer of a compound of formula (I).

In accordance with a second aspect of the present invention there is provided a pharmaceutical composition comprising a compound of the first aspect of the present invention and a pharmaceutically acceptable excipient and/or carrier and/or diluent.

In accordance with a third aspect of the present invention there is provided a compound or pharmaceutical composition of any aspect of the present invention, including all embodiments thereof, for use in a therapeutic method for treating a microbial infection and/or for treating inflammation and/or for reducing the formation of blood clots and/or for treating a wound and/or for treating cystic fibrosis and/or for treating epidermolysis bullosa.

In accordance with a fourth aspect of the present invention there is provided a use of a compound or pharmaceutical composition of any aspect of the present invention, including all embodiments thereof, in the manufacture of a medicament for treating a microbial infection and/or for treating inflammation and/or for reducing the formation of blood clots and/or for treating a wound and/or for treating cystic fibrosis and/or for treating epidermolysis bullosa.

In accordance with a fifth aspect of the present invention there is provided a therapeutic method for treating a microbial infection and/or for treating inflammation and/or for reducing the formation of blood clots and/or for treating a wound and/or for treating cystic fibrosis and/or for treating epidermolysis bullosa, wherein the method comprises administering a compound or pharmaceutical composition of any aspect of the present invention, including all embodiments thereof, to a subject.

In accordance with a sixth aspect of the present invention there is provided a non-therapeutic use of a compound or pharmaceutical composition of any aspect of the present invention, including all embodiments thereof, as an antimicrobial agent and/or as an anti-inflammatory agent and/or as an anti-thrombotic agent. For example, there is provided herein an in vitro use of a compound or pharmaceutical composition of any aspect of the present invention, including all embodiments thereof, as an antimicrobial agent and/or as an anti-inflammatory agent and/or as an anti-thrombotic agent.

In accordance with a seventh aspect of the present invention there is provided a method for making a compound of the first aspect of the present invention. The method may, for example, proceed via the following reaction scheme:

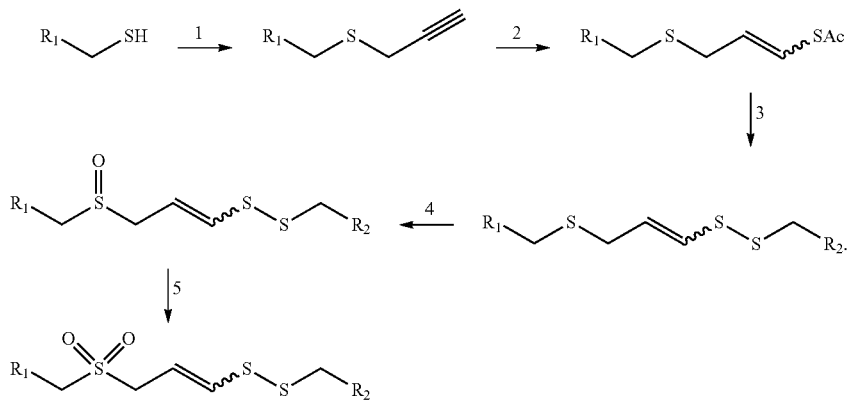

The details, examples and preferences provided in relation to any particulate one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

BRIEF DESCRIPTION OF THE FIGURES

The present invention may be described with reference to the following non-limiting Figures in which.

DETAILED DESCRIPTION

Compounds and Pharmaceutical Compositions

Figure 1:
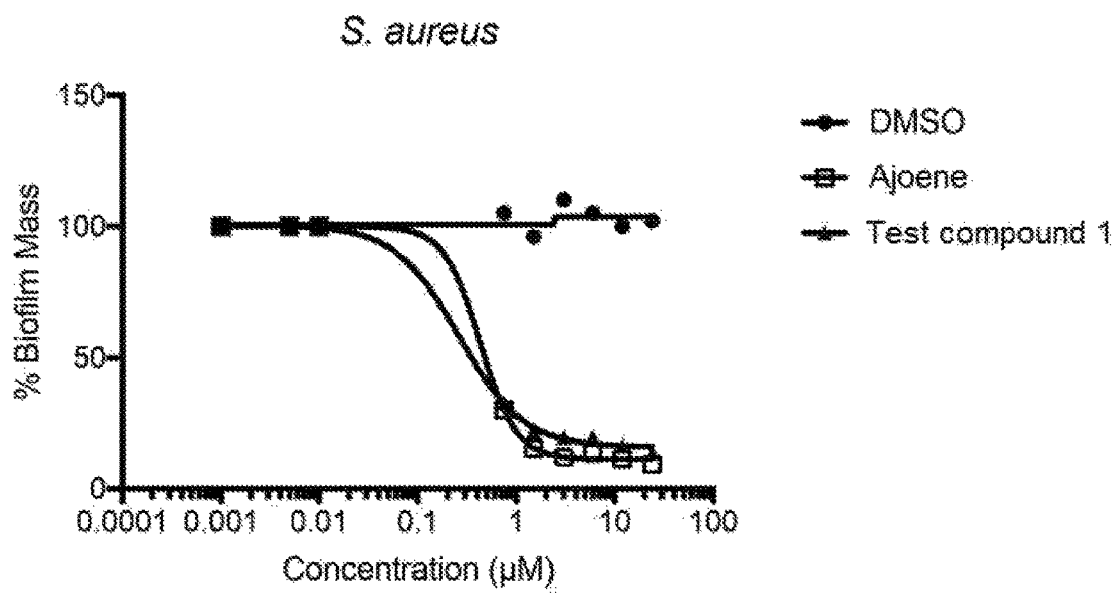
FIG. 1 shows the plot of concentration versus % *S. aureus* biofilm mass for the compound of formula (I) tested in example 4 compared to ajoene and DMSO.

The present invention is based, at least in part, on the surprising finding that compounds of formula (I) have an advantageous antimicrobial and/or wound healing activity. For example, embodiments of the present invention are based on the surprising finding that compounds of formula (I) provide an improved antimicrobial and/or wound healing activity in comparison to other organosulfur compounds.

Hereinafter, the invention shall be described according to preferred embodiments of the present invention and by referring to the accompanying description. However, it is to be understood that limiting the description to the preferred embodiments of the invention is merely to facilitate discussion of the present invention and it is envisioned that those skilled in the art may devise various modifications without departing from the scope of the appended claims.

The terms generally used hereinbefore and hereinafter have for preference the meanings indicated below, unless indicated otherwise, whereby more specific meanings may be used independently of one another in preferred embodiments of the present inventions instead of the general definitions, these more specific significances describing especially preferred embodiments of the invention.

Where the term "at least one" or "one or more" occurs hereinbefore and hereinafter, this signifies for example one to ten, for preference one to three, and in particular one or, further, two of the features enumerated, such as components. Where ranges are indicated, such as weight percentage ranges, these include the limit values indicated; thus, for example, "between X and Y" signifies "from and including X up to and including Y".

The compounds of the present invention are according to formula (I):

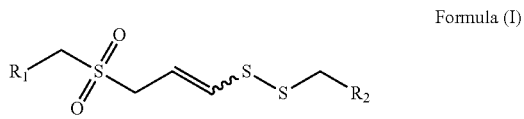

Formula (I)

wherein $R_1$ is phenyl, substituted phenyl, cycloalkyl, substituted cycloalkyl, heterocyclyl, or substituted heterocyclyl; and $R_2$ is phenyl, substituted phenyl, cycloalkyl, substituted cycloalkyl or alkenyl.

The compounds of the present invention may be according to formula (IA) and/or according to formula (IB).

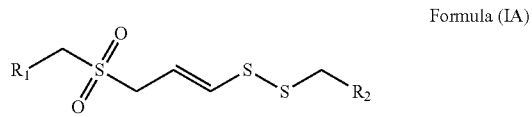

Formula (IA)

Formula (IB)

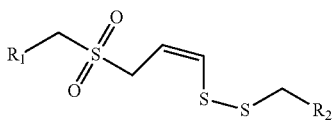

wherein
R₁ is phenyl, substituted phenyl, cycloalkyl, substituted cycloalkyl, heterocyclyl, or substituted heterocyclyl; and R₂ is phenyl, substituted phenyl, cycloalkyl, substituted cycloalkyl, or alkenyl.

The term "phenyl" as used herein refers to a radical having the formula $C_6H_5$ that is derived from benzene by the removal of a hydrogen atom.

The term "substituted phenyl" as used herein refers to a radical that is derived from benzene by the removal of a hydrogen atom, wherein one or more of the remaining hydrogen atoms on the benzene ring is replaced by a functional group. The substituted phenyl may, for example, comprise one, two, three, four, or five functional groups. The substituted phenyl may, for example, comprise one or two functional groups. The substituted phenyl may, for example, comprise only one functional group. The substitution may, for example, occur at the meta-, ortho-, or para-position on the phenyl ring.

Each functional group may, for example, independently be selected from an alkyl group, a haloalkyl group, an ester group, an alkoxy group, a halogen group, an alkylsulphone group, a haloalkoxy group, or an amine group. Thus, the substituted phenyl may, for example, be an alkylphenyl, a haloalkylphenyl, an alkylbenzoate, an alkoxyphenyl, a halophenyl, an alkylphenyl sulphone, a haloalkoxyphenyl, or an aminophenyl.

The term "alkyl" used herein refers to a radical derived from a saturated linear or branched hydrocarbon by removal of a hydrogen atom. The alkyl may, for example, comprise from 1 to 8 carbon atoms or from 1 to 4 carbon atoms or from 1 to 2 carbon atoms.

The term "haloalkyl" used herein refers to a radical derived from a saturated linear or branched hydrocarbon by removal of a hydrogen atom, where one or more of the remaining hydrogen atoms of the alkyl group is replaced by a halogen. The haloalkyl may, for example, comprise from 1 to 8 carbon atoms or from 1 to 4 carbon atoms or from 1 to 2 carbon atoms. The haloalkyl may, for example, comprise from 1 to 8 halogen atoms or from 1 to 5 halogen atoms or from 1 to 4 halogen atoms or from 1 to 3 halogen atoms. The halogen atoms may each, independently, be selected from iodine, chlorine, bromine, and fluorine. The haloalkyl may, for example, be a halomethyl. For example, the haloalkyl may be a trihalomethyl. For example, the haloalkyl may be trifluoromethyl. Thus, the haloalkylphenyl may, for example, be halomethylphenyl. The haloalkylphenyl may, for example, be trihalomethylphenyl. The haloalkylphenyl may, for example, be trifluoromethyl phenyl. The trifluoromethyl group may, for example, occur at the para-position of the phenyl ring.

The term "ester" used herein refers to a group having the formula —C(═O)OR, wherein R is an alkyl group. The alkyl is a saturated linear or branched chain hydrocarbon. The alkyl may, for example, comprise from 1 to 8 carbon atoms or from 1 to 4 carbon atoms or from 1 to 2 carbon atoms. The alkyl may, for example, contain 1 carbon atom (a methyl group) such that the alkyl benzoate is methylbenzoate. The ester group may, for example, occur at the para-position of the phenyl ring.

The term "alkoxy" used herein refers to a group having the formula —OR, wherein R is an alkyl group. The alkyl is a saturated linear or branched chain hydrocarbon. The alkyl may, for example, comprise from 1 to 8 carbon atoms or from 1 to 4 carbon atoms or from 1 to 2 carbon atoms. The alkyl may, for example, contain 1 carbon atom (a methyl group) such that the alkoxyphenyl is methoxyphenyl. The alkoxy may, for example, occur at the meta-, ortho-, or para-positions of the phenyl ring.

The term "haloalkoxy" used herein refers to a group having the formula —OR, wherein R is an alkyl group, wherein one or more of the hydrogen atoms of the alkyl group is replaced by a halogen. The haloalkoxy may, for example, comprise from 1 to 8 carbon atoms or from 1 to 4 carbon atoms or from 1 to 2 carbon atoms. The haloalkoxy may, for example, comprise from 1 to 8 halogen atoms or from 1 to 5 halogen atoms or from 1 to 4 halogen atoms or from 1 to 3 halogen atoms. The halogen atoms may each, independently, be selected from iodine, chlorine, bromine, and fluorine. The haloalkoxy group may, for example, occur at the para-position of the phenyl ring. The haloalkoxy may, for example, be fluoroalkoxy. The haloalkoxy may, for example, be a halomethoxy. For example, the haloalkoxy may be a trihalomethoxy. For example, the haloalkoxy may be trifluoromethoxy. Thus, the haloalkoxyphenyl may, for example, be halomethoxyphenyl. The haloalkoxyphenyl may, for example, be trihalomethoxyphenyl. The haloalkoxyphenyl may, for example, be trifluoromethoxy phenyl. The trifluoromethoxy group may, for example, occur at the para-position of the phenyl ring.

The term "halo" or "halogen" used herein refers to any of fluorine, chlorine, bromine, iodine, and astatine. In certain embodiments, the halogen is selected from fluorine, chlorine, bromine, and iodine. In certain embodiments, the halogen is selected from fluorine, chlorine, and bromine. In certain embodiments, the halogen is fluorine or chlorine. In certain embodiments, the halogen is fluorine. Thus, the substituted phenyl may be fluorophenyl. The halogen may, for example, occur at the para-position of the phenyl ring.

The term "alkylsulphone" used herein refers to a group having the formula —S(O)(O)R, wherein R is an alkyl group. The alkyl group may, for example, comprise from 1 to 8 carbon atoms or from 1 to 4 carbon atoms or from 1 to 2 carbon atoms. The alkyl may, for example, contain 1 carbon atom (a methyl group) such that the alkylsulphone is methylsulphone (thus the substituted phenyl would be methyl phenyl sulphone). The alkylsulphone may, for example, occur at the para-position of the phenyl ring.

The term "amine" used herein refers to a group having the formula —NRR', wherein R and R' are each independently selected from hydrogen, halogen, alkyl, haloalkyl, alkoxy, haloalkoxy, carbonyl (—C(O)R" where R" is an alkyl group), ester, or alkylsulphone. The term "aminophenyl" used herein therefore refers to a radical that is derived from benzene by the removal of a hydrogen atom, wherein one or more of the remaining hydrogen atoms on the benzene ring is replaced by an amine group as defined herein. In certain embodiments, R and R' of the amino group are each independently selected from hydrogen and alkyl. In certain embodiments, both R and R' are alkyl groups, for example both R and R' may be alkyl groups comprising from 1 to 4 carbon atoms. In certain embodiments, both R and R' are methyl. Thus, the substituted phenyl may be dimethylaminophenyl. In certain embodiments, both R and R' may be hydrogen.

When $R_1$ is substituted phenyl, the substituted phenyl may preferably be a halophenyl, a haloalkylphenyl, an alkoxyphenyl, or an alkyl phenyl sulphone. The halophenyl may, for example, be iodophenyl, chlorophenyl, bromophenyl, or fluorophenyl, preferably fluorophenyl. The haloalkylphenyl may, for example, be halomethylphenyl, for example trihalomethylphenyl, for example trifluoromethylphenyl. The alkoxyphenyl may, for example, be methoxyphenyl, ethoxyphenyl, or propoxyphenyl, preferably methoxyphenyl. The alkyl phenyl sulphone may, for example, be methyl phenyl sulphone, ethyl phenyl sulphone, or propyl phenyl sulphone, preferably methyl phenyl sulphone.

When $R_1$ is substituted phenyl, the substituted phenyl may preferably be a haloalkylphenyl. The halogen may, for example, be one or more of iodine, chlorine, bromine, or fluorine. The halogen may, for example, be fluorine. Where more than one halogen atoms are present, all the halogen atoms may be the same. The haloalkylphenyl may, for example, be halomethylphenyl. The halomethylphenyl may, for example, be trihalomethylphenyl. The trihalomethylphenyl may, for example, be trifluoromethylphenyl.

When $R_2$ is substituted phenyl, the substituted phenyl may haloalkylphenyl, alkylbenzoate or alkoxyphenyl. In the haloalkylphenyl, the halogen may, for example, be one or more of iodine, chlorine, bromine, or fluorine. Where more than one halogen atoms are present, all the halogen atoms may be the same. The haloalkylphenyl may, for example, be halomethylphenyl. The halomethylphenyl may, for example, be trihalomethylphenyl. The trihalomethylphenyl may, for example, be trifluoromethylphenyl. The allylbenzoate may, for example, be methylbenzoate, ethylbenzoate, or propylbenzoate. The alkylbenzoate may, for example, be methylbenzoate. The alkoxyphenyl may, for example, be methoxyphenyl, ethoxyphenyl, or propoxyphenyl. The alkoxyphenyl may, for example, be methoxyphenyl.

The term "cycloalkyl" as used herein refers to a radical derived from a monocyclic saturated hydrocarbon by the removal of a hydrogen atom. The cycloalkyl may, for example, comprise from 3 to 10 carbon atoms or from 3 to 8 carbon atoms or from 3 to 6 carbon atoms or from 3 to 5 carbon atoms or from 3 to 4 carbon atoms. The cycloalkyl may, for example, be cyclopropyl or cyclobutyl or cyclopentyl. The cycloalkyl may, for example, be cyclopropyl.

The term "substituted cycloalkyl" as used herein refers to a radical derived from a monocyclic saturated hydrocarbon by the removal of a hydrogen atom, wherein one or more of the remaining hydrogen atoms on the monocyclic saturated hydrocarbon is replaced by a functional group. The substituted cycloalkyl may, for example, comprise one, two, three, four, or five functional groups. The substituted cycloalkyl may, for example, comprise one or two functional groups. The substituted cycloalkyl may, for example, comprise only one functional group. The substitution may, for example, occur at the meta-, ortho-, or para-position on the phenyl ring. Each functional group may, for example, independently be selected from an alkyl group, a haloalkyl group, an ester group, an alkoxy group, a halogen group, an alkylsulphone group, a haloalkoxy group, or an amino group, as defined above.

The term "heterocyclyl" used herein refers to a radical derived from a saturated or unsaturated cyclic structure that has atoms of at least two different elements as members of the ring by removal of a hydrogen atom. The heterocyclyl may, for example, be a heteroaryl. The heterocyclyl may, for example, have one or more carbon atoms and one or more atoms selected from nitrogen, oxygen, and sulphur, as members of the ring. The heterocyclyl may, for example, be isoxazole, furan, pyrimidine, or thiophene. For example, the heterocyclyl may be furan or thiophene.

The term "substituted heterocyclyl" used herein refers to a radical derived from a saturated or unsaturated cyclic structure that has atoms of at least two different elements as members of the ring, wherein one or more of the remaining hydrogen atoms on the heterocyclyl is replaced by a functional group. The substituted heterocyclyl may, for example, be a substituted heteroaryl. The substituted heterocyclyl may, for example, comprise one, two, three, four, or five functional groups. The substituted heterocyclyl may, for example, comprise one or two functional groups. The substituted heterocyclyl may, for example, comprise only one functional group. Each functional group may, for example, be an alkyl group (e.g. methyl) or an alkoxy group (e.g. methoxy). The substitution may, for example, occur on a carbon atom. The heterocyclyl may, for example, include an oxazole ring, an isoxazole ring, a furan ring, a pyrimidine ring, or a thiophene ring. The substituted heterocyclyl may, for example, be a substituted furan ring or a substituted thiophene ring. Each functional group may, for example, independently be selected from an alkyl group, a haloalkyl group, an ester group, an alkoxy group, a halogen group, a sulphonyl group (e.g. an alkylsulphonyl) group, a haloalkoxy group, or an amine group.

The term "alkenyl" as used herein refers to a radical derived from an unsaturated straight or branched chain hydrocarbon. The alkenyl group may, for example, contain 1, 2, or 3 carbon-carbon double bonds. For example, the alkenyl group may contain 1 carbon-carbon double bond. The alkenyl may, for example, comprise from 2 to 8 carbon atoms or from 2 to 4 carbon atoms or from 2 to 3 carbon atoms. The alkenyl may, for example, be ethenyl.

$R_1$ may, for example, be selected from phenyl, halophenyl, haloalkylphenyl, alkoxyphenyl, alkyl phenyl sulphone, cycloalkyl, and substituted cycloalkyl. For example, $R_1$ may be selected from phenyl, halophenyl, halomethylphenyl, alkoxyphenyl, alkylphenyl sulphone, cycloalkyl, and substituted cycloalkyl. For example, $R_1$ may be selected from phenyl, fluorophenyl, trifluomethylphenyl, methoxyphenyl, methyl phenyl sulphone, cycloalkyl and substituted cycloalkyl. The alkyl group of the haloalkylphenyl may, for example, contain from 1 to 4 carbon atoms, for example 1 or 2 carbon atoms. The cycloalkyl or cycloalkyl part of the substituted cycloalkyl may, for example, contain from 3 to 6 carbon atoms or from 3 to 4 carbon atoms. The cycloalkyl or substituted cycloalkyl may, for example, be cyclopropyl or substituted cyclopropyl.

$R_1$ may, for example, be selected from phenyl, halophenyl, haloalkylphenyl, alkoxyphenyl, alkylphenyl sulphone, cycloalkyl, substituted cycloalkyl, heterocyclyl, and substituted heterocyclyl. For example, $R_1$ may be selected from phenyl, halophenyl, halomethylphenyl, alkoxyphenyl, alkylphenyl sulphone, cycloalkyl, substituted cycloalkyl, heterocyclyl, and substituted heterocyclyl. For example, $R_1$ may be selected from phenyl, fluorophenyl, trifluomethylphenyl, methoxyphenyl, methylphenyl sulphone, cycloalkyl, substituted cycloalkyl, heterocyclyl, and substituted heterocyclyl. The alkyl group of the haloalkylphenyl may, for example, contain from 1 to 4 carbon atoms, for example 1 or 2 carbon atoms. The cycloalkyl or cycloalkyl part of the substituted cycloalkyl may, for example, contain from 3 to 6 carbon atoms or from 3 to 4 carbon atoms. The cycloalkyl or substituted cycloalkyl may, for example, be cyclopropyl or substituted cyclopropyl. The heterocyclyl or heterocyclyl part of the substituted heterocyclyl may, for example, contain from 3 to 6 carbon atoms and 1 or 2 heteroatoms (e.g.

oxygen or sulphur). For example, the heterocyclyl or heterocyclyl part of the substituted heterocyclyl may, for example, contain from 4 or 5 carbon atoms and 1 heteroatom (e.g. oxygen or sulphur). The heterocyclyl or substituted heterocyclyl may, for example, be furan, thiophene, substituted furan or substituted thiophene.

$R_1$ may, for example, be selected from phenyl, substituted phenyl, and cycloalkyl. $R_1$ may, for example, be selected from phenyl, halophenyl, haloalkylphenyl, alkoxyphenyl, alkylphenyl sulphone, and cycloalkyl. For example, $R_1$ may be selected from phenyl, halophenyl, halomethylphenyl, alkoxyphenyl, alkyl phenyl sulphone, and cycloalkyl. For example, $R_1$ may be selected from phenyl, fluorophenyl, trifluomethylphenyl, methoxyphenyl, methylphenyl sulphone, and cycloalkyl. The alkyl group of the haloalkylphenyl may, for example, contain from 1 to 4 carbon atoms, for example 1 or 2 carbon atoms. The cycloalkyl may, for example, contain from 3 to 6 carbon atoms or from 3 to 4 carbon atoms. The cycloalkyl may, for example, be cyclopropyl.

$R_1$ may, for example, be selected from phenyl, substituted phenyl, and cycloalkyl. $R_1$ may, for example, be selected from phenyl, halophenyl, haloalkylphenyl, alkoxyphenyl, alkylphenyl sulphone, cycloalkyl and heterocyclyl. For example, $R_1$ may be selected from phenyl, halophenyl, halomethylphenyl, alkoxyphenyl, alkyl phenyl sulphone, cycloalkyl, and heterocyclyl. For example, $R_1$ may be selected from phenyl, fluorophenyl, trifluomethylphenyl, methoxyphenyl, methylphenyl sulphone, and cycloalkyl. The alkyl group of the haloalkylphenyl may, for example, contain from 1 to 4 carbon atoms, for example 1 or 2 carbon atoms. The cycloalkyl may, for example, contain from 3 to 6 carbon atoms or from 3 to 4 carbon atoms. The cycloalkyl may, for example, be cyclopropyl. The heterocyclyl may, for example, contain from 3 to 6 carbon atoms and 1 or 2 heteroatoms (e.g. oxygen or sulphur). The heterocyclyl may, for example, contain from 4 or 5 carbon atoms and 1 heteroatom (e.g. oxygen or sulphur). The heterocyclyl may, for example, be furan or thiophene.

$R_1$ may, for example, be phenyl, substituted phenyl, cycloalkyl or heterocyclyl. $R_1$ may, for example, be phenyl, halophenyl, haloalkylphenyl, alkoxyphenyl, alkylphenyl sulphone, cycloalkyl or heterocyclyl. $R_1$ may, for example, be phenyl or substituted phenyl, for example phenyl, halophenyl, haloalkylphenyl, alkoxyphenyl, or alkylphenyl sulphone. For example, $R_1$ may be phenyl or cycloalkyl. For example, $R_1$ may be substituted phenyl or cycloalkyl, for example halophenyl, haloalkylphenyl, alkoxyphenyl, alkylphenyl sulphone, or cycloalkyl. For example, $R_1$ may be phenyl. For example, $R_1$ may be substituted phenyl. For example, $R_1$ may be cycloalkyl. For example, $R_1$ may be substituted cycloalkyl. For example, $R_1$ may be heterocyclyl. For example, $R_1$ may be substituted heterocyclyl. The alkyl group of the haloalkylphenyl may, for example, contain from 1 to 4 carbon atoms, for example 1 or 2 carbon atoms. The cycloalkyl or cycloalkyl part of the substituted cycloalkyl may, for example, contain from 3 to 6 carbon atoms or from 3 to 4 carbon atoms. The cycloalkyl or substituted cycloalkyl may, for example, be cyclopropyl or substituted cycloalkyl. The heterocyclyl or heterocyclyl part of the substituted heterocyclyl may, for example, contain from 3 to 6 carbon atoms and 1 or 2 heteroatoms (e.g. oxygen or sulphur). For example, the heterocyclyl or heterocyclyl part of the substituted heterocyclyl may, for example, contain from 4 or 5 carbon atoms and 1 heteroatom (e.g. oxygen or sulphur). The heterocyclyl or substituted heterocyclyl may, for example, be furan, thiophene, substituted furan or substituted thiophene.

$R_2$ may, for example, be selected from phenyl, haloalkylphenyl, alkylbenzoate, alkoxyphenyl, cycloalkyl, substituted cycloalkyl, and alkenyl. For example, $R_2$ may be selected from phenyl, halomethylphenyl, alkylbenzoate, alkoxyphenyl, cycloalkyl, substituted cycloalkyl, and alkenyl. For example, $R_2$ may be selected from phenyl, trifluoromethylphenyl, alkylbenzoate, alkoxyphenyl, cycloalkyl, substituted cycloalkyl, and alkenyl. The alkyl group of the haloalkylphenyl, alkylbenzoate, and alkoxyphenyl may, for example, each contain from 1 to 4 carbon atoms, for example 1 or 2 carbon atoms. The cycloalkyl may, for example, contain from 3 to 6 carbon atoms or from 3 to 4 carbon atoms. The cycloalkyl may, for example, be cyclopropyl. The alkenyl may, for example, contain from 2 to 4 carbon atoms and one double bond, for example from 2 to 3 carbon atoms and one double bond. The alkenyl may, for example, be ethenyl. $R_2$ may, for example, be selected from phenyl, substituted phenyl, cycloalkyl, and alkenyl. $R_2$ may, for example, be selected from phenyl, substituted phenyl, cyclopropyl, and alkenyl. For example, $R_2$ may be selected from phenyl, haloalkylphenyl, alkylbenzoate, alkoxyphenyl, cyclopropyl, and alkenyl. For example, $R_2$ may be selected from phenyl, halomethylphenyl, alkylbenzoate, alkoxyphenyl, cyclopropyl, and alkenyl. For example, $R_2$ may be selected from phenyl, trifluoromethylphenyl, alkylbenzoate, alkoxyphenyl, cyclopropyl, and alkenyl. The alkyl group of the haloalkylphenyl, alkylbenzoate, and alkoxyphenyl may, for example, each contain from 1 to 4 carbon atoms, for example 1 or 2 carbon atoms. The cycloalkyl may, for example, contain from 3 to 6 carbon atoms or from 3 to 4 carbon atoms. The cycloalkyl may, for example, be cyclopropyl. The alkenyl may, for example, contain from 2 to 4 carbon atoms and one double bond, for example from 2 to 3 carbon atoms and one double bond. The alkenyl may, for example, be ethenyl.

$R_2$ may, for example, be selected from phenyl, substituted phenyl, cycloalkyl, substituted cycloalkyl, and ethenyl. $R_2$ may, for example, be selected from phenyl, substituted phenyl, cycloalkyl, and ethenyl. For example, $R_2$ may be selected from phenyl, haloalkylphenyl, alkylbenzoate, alkoxyphenyl, cycloalkyl, and ethenyl. For example, $R_2$ may be selected from phenyl, halomethylphenyl, alkylbenzoate, alkoxyphenyl, cycloalkyl, and ethenyl. For example, $R_2$ may be selected from phenyl, trifluoromethylphenyl, alkylbenzoate, alkoxyphenyl, cycloalkyl, and ethenyl. The alkyl group of the haloalkylphenyl, alkylbenzoate, and alkoxyphenyl may, for example, each contain from 1 to 4 carbon atoms, for example 1 or 2 carbon atoms. The cycloalkyl may, for example, contain from 3 to 6 carbon atoms or from 3 to 4 carbon atoms. The cycloalkyl may, for example, be cyclopropyl.

$R_2$ may, for example, be selected from phenyl, substituted phenyl, cyclopropyl, and ethenyl. $R_2$ may, for example, be selected from phenyl, haloalkylphenyl, alkylbenzoate, alkoxyphenyl, cycloalkyl, and ethenyl. $R_2$ may, for example, be selected from phenyl, haloalkylphenyl, alkylbenzoate, alkoxyphenyl, cyclopropyl, and ethenyl. The alkyl group of the haloalkylphenyl, alkylbenzoate, and alkoxyphenyl may, for example, each contain from 1 to 4 carbon atoms, for example 1 or 2 carbon atoms. The cycloalkyl may, for example, contain from 3 to 6 carbon atoms or from 3 to 4 carbon atoms. The cycloalkyl may, for example, be cyclopropyl.

In certain embodiments, $R_1$ is phenyl, substituted phenyl, or cycloalkyl and $R_2$ is phenyl, substituted phenyl, cycloalkyl, or alkenyl. In certain embodiments, $R_1$ is phenyl, halophenyl, haloalkylphenyl, alkoxyphenyl, alkyl phenyl sulphone, or cycloalkyl and $R_2$ is phenyl, substituted phenyl, cycloalkyl, or alkenyl. In certain embodiments, $R_1$ is phenyl, halophenyl, haloalkylphenyl, alkoxyphenyl, alkylphenyl sulphone or cycloalkyl and $R_2$ is phenyl, haloalkylphenyl, alkylbenzoate, alkoxyphenyl, cycloalkyl, or alkenyl. In certain embodiments, $R_1$ is phenyl, haloalkylphenyl, or cycloalkyl and $R_2$ is phenyl, substituted phenyl, cycloalkyl, or alkenyl. In certain embodiments, $R_1$ is phenyl, haloalkylphenyl, or cycloalkyl and $R_2$ is phenyl, haloalkylphenyl, alkylbenzoate, alkoxyphenyl, cycloalkyl, or alkenyl. In certain embodiments, $R_1$ is phenyl, halophenyl, haloalkylphenyl, alkoxyphenyl, alkylphenyl sulphone or cycloalkyl and $R_2$ is phenyl, substituted phenyl, cycloalkyl, or alkenyl, wherein when $R_1$ is haloalkylphenyl, alkoxyphenyl or alkylphenyl sulphone, the alkyl group comprises 1 to 4 carbon atoms, for example 1 or 2 carbon atoms. In certain embodiments, $R_1$ is phenyl, halophenyl, haloalkylphenyl, alkoxyphenyl, alkylphenyl sulphone or cycloalkyl and $R_2$ is phenyl, haloalkylphenyl, alkylbenzoate, alkoxyphenyl, cycloalkyl, or alkenyl, wherein when $R_1$ and/or $R_2$ is haloalkylphenyl, alkylbenzoate, alkoxyphenyl or alkylphenyl sulphone, the alkyl group comprises from 1 to 4 carbon atoms, for example 1 or 2 carbon atoms.

In certain embodiments, $R_1$ is phenyl, substituted phenyl, cycloalkyl, or heterocyclyl and $R_2$ is phenyl, substituted phenyl, cycloalkyl, or alkenyl. In certain embodiments, $R_1$ is phenyl, halophenyl, haloalkylphenyl, alkoxyphenyl, alkyl phenyl sulphone, cycloalkyl, or heterocyclyl and $R_2$ is phenyl, substituted phenyl, cycloalkyl, or alkenyl. In certain embodiments, $R_1$ is phenyl, halophenyl, haloalkylphenyl, alkoxyphenyl, alkylphenyl sulphone, cycloalkyl, or heterocyclyl and $R_2$ is phenyl, haloalkylphenyl, alkylbenzoate, alkoxyphenyl, cycloalkyl, or alkenyl. In certain embodiments, $R_1$ is phenyl, haloalkylphenyl, cycloalkyl, or heterocyclyl and $R_2$ is phenyl, substituted phenyl, cycloalkyl, or alkenyl. In certain embodiments, $R_1$ is phenyl, haloalkylphenyl, cycloalkyl, or heterocyclyl and $R_2$ is phenyl, haloalkylphenyl, alkylbenzoate, alkoxyphenyl, cycloalkyl, or alkenyl. In certain embodiments, $R_1$ is phenyl, halophenyl, haloalkylphenyl, alkoxyphenyl, alkylphenyl sulphone, cycloalkyl, or heterocyclyl and $R_2$ is phenyl, substituted phenyl, cycloalkyl, or alkenyl, wherein when $R_1$ is haloalkylphenyl, alkoxyphenyl or alkylphenyl sulphone, the alkyl group comprises 1 to 4 carbon atoms, for example 1 or 2 carbon atoms. In certain embodiments, $R_1$ is phenyl, halophenyl, haloalkylphenyl, alkoxyphenyl, alkylphenyl sulphone, cycloalkyl, or heterocyclyl and $R_2$ is phenyl, haloalkylphenyl, alkylbenzoate, alkoxyphenyl, cycloalkyl, or alkenyl, wherein when $R_1$ and/or $R_2$ is haloalkylphenyl, alkylbenzoate, alkoxyphenyl or alkylphenyl sulphone, the alkyl group comprises from 1 to 4 carbon atoms, for example 1 or 2 carbon atoms.

In certain embodiments, $R_1$ is phenyl, substituted phenyl, or cycloalkyl and $R_2$ is phenyl, substituted phenyl, cycloalkyl, or alkenyl, wherein when $R_1$ and/or $R_2$ is cycloalkyl, the cycloalkyl contains from 3 to 6 carbon atoms, for example 3 or 4 carbon atoms, for example 3 carbon atoms. In certain embodiments, $R_1$ is phenyl, halophenyl, haloalkylphenyl, alkoxyphenyl, alkylphenyl sulphone or cycloalkyl and $R_2$ is phenyl, haloalkylphenyl, alkylbenzoate, alkoxyphenyl, cycloalkyl, or alkenyl, wherein when $R_1$ and/or $R_2$ is cycloalkyl, the cycloalkyl contains from 3 to 6 carbon atoms, for example 3 or 4 carbon atoms. In certain embodiments, $R_1$ is phenyl, halophenyl, haloalkylphenyl, alkoxyphenyl, alkylphenyl sulphone or cycloalkyl and $R_2$ is phenyl, haloalkylphenyl, alkylbenzoate, alkoxyphenyl, cycloalkyl, or alkenyl, wherein when $R_1$ and/or $R_2$ is cycloalkyl, the cycloalkyl contains from 3 to 6 carbon atoms, for example 3 or 4 carbon atoms and when $R_1$ and/or $R_2$ is haloalkylphenyl, alkylbenzoate, alkoxyphenyl, or alkylphenyl sulphone, the alkyl group comprises from 1 to 4 carbon atoms, for example 1 or 2 carbon atoms. In certain embodiments, $R_1$ is phenyl, halophenyl, haloalkylphenyl, alkoxyphenyl, alkylphenyl sulphone or cycloalkyl and $R_2$ is phenyl, haloalkylphenyl, alkylbenzoate, alkoxyphenyl, cycloalkyl, or alkenyl, wherein when $R_1$ and/or $R_2$ is cycloalkyl, the cycloalkyl contains from 3 to 6 carbon atoms, for example 3 or 4 carbon atoms and when $R_2$ is alkenyl, the alkenyl contains one double bond and from 2 to 6 carbon atoms, for example 2 or 3 carbon atoms. In certain embodiments, $R_1$ is phenyl, halophenyl, haloalkylphenyl, alkoxyphenyl, alkyl phenyl sulphone, or cycloalkyl and $R_2$ is phenyl, haloalkylphenyl, alkylbenzoate, alkoxyphenyl, cycloalkyl, or alkenyl, wherein when $R_1$ and/or $R_2$ is cycloalkyl, the cycloalkyl contains from 3 to 6 carbon atoms, for example 3 or 4 carbon atoms and when $R_2$ is alkenyl, the alkenyl contains one double bond and from 2 to 6 carbon atoms, for example 2 or 3 carbon atoms and when $R_1$ and/or $R_2$ is haloalkylphenyl, alkylbenzoate, alkoxyphenyl, or alkylphenyl sulphone, the haloalkyl or alkyl group comprises from 1 to 4 carbon atoms, for example 1 or 2 carbon atoms.

In certain embodiments, $R_1$ is phenyl, substituted phenyl, cycloalkyl, or heterocyclyl and $R_2$ is phenyl, substituted phenyl, cycloalkyl, or alkenyl, wherein when $R_1$ and/or $R_2$ is cycloalkyl, the cycloalkyl contains from 3 to 6 carbon atoms, for example 3 or 4 carbon atoms, for example 3 carbon atoms, and/or wherein $R_1$ is heterocyclyl, the heterocyclyl contains from 3 to 6 carbon atoms and 1 or 2 heteroatoms (e.g. oxygen or sulphur), for example, from 4 or 5 carbon atoms and 1 heteroatom (e.g. oxygen or sulphur), for example wherein the heterocyclyl is furan or thiophene. In certain embodiments, $R_1$ is phenyl, halophenyl, haloalkylphenyl, alkoxyphenyl, alkylphenyl sulphone, cycloalkyl, or heterocyclyl and $R_2$ is phenyl, haloalkylphenyl, alkylbenzoate, alkoxyphenyl, cycloalkyl, or alkenyl, wherein when $R_1$ and/or $R_2$ is cycloalkyl, the cycloalkyl contains from 3 to 6 carbon atoms, for example 3 or 4 carbon atoms, and/or wherein when $R_1$ is heterocyclyl, the heterocyclyl contains from 3 to 6 carbon atoms and 1 or 2 heteroatoms (e.g. oxygen or sulphur), for example, from 4 or 5 carbon atoms and 1 heteroatom (e.g. oxygen or sulphur), for example wherein the heterocyclyl is furan or thiophene.

In certain embodiments, $R_1$ is phenyl, halophenyl, haloalkylphenyl, alkoxyphenyl, alkylphenyl sulphone, cycloalkyl, or heterocyclyl and $R_2$ is phenyl, haloalkylphenyl, alkylbenzoate, alkoxyphenyl, cycloalkyl, or alkenyl, wherein when $R_1$ and/or $R_2$ is cycloalkyl, the cycloalkyl contains from 3 to 6 carbon atoms, for example 3 or 4 carbon atoms and when $R_1$ and/or $R_2$ is haloalkylphenyl, alkylbenzoate, alkoxyphenyl, or alkylphenyl sulphone, the alkyl group comprises from 1 to 4 carbon atoms, for example 1 or 2 carbon atoms, and/or wherein when $R_1$ is heterocyclyl, the heterocyclyl contains from 3 to 6 carbon atoms and 1 or 2 heteroatoms (e.g. oxygen or sulphur), for example, from 4 or 5 carbon atoms and 1 heteroatom (e.g. oxygen or sulphur), for example wherein the heterocyclyl is furan or thiophene.

In certain embodiments, $R_1$ is phenyl, halophenyl, haloalkylphenyl, alkoxyphenyl, alkylphenyl sulphone, cycloalkyl, or heterocyclyl and $R_2$ is phenyl, haloalkylphenyl, alkylbenzoate, alkoxyphenyl, cycloalkyl, or alkenyl, wherein when $R_1$ and/or $R_2$ is cycloalkyl, the cycloalkyl contains from 3 to 6 carbon atoms, for example 3 or 4 carbon atoms and/or when R₂ is alkenyl, the alkenyl contains one double bond and from 2 to 6 carbon atoms, for example 2 or 3 carbon atoms and/or when wherein R₁ is heterocyclyl, the heterocyclyl contains from 3 to 6 carbon atoms and 1 or 2 heteroatoms (e.g. oxygen or sulphur), for example, from 4 or 5 carbon atoms and 1 heteroatom (e.g. oxygen or sulphur), for example wherein the heterocyclyl is furan or thiophene. In certain embodiments, R₁ is phenyl, halophenyl, haloalkylphenyl, alkoxyphenyl, alkyl phenyl sulphone, cycloalkyl, or heterocyclyl and R₂ is phenyl, haloalkylphenyl, alkylbenzoate, alkoxyphenyl, cycloalkyl, or alkenyl, wherein when R₁ and/or R₂ is cycloalkyl, the cycloalkyl contains from 3 to 6 carbon atoms, for example 3 or 4 carbon atoms and when R₂ is alkenyl, the alkenyl contains one double bond and from 2 to 6 carbon atoms, for example 2 or 3 carbon atoms and when R₁ and/or R₂ is haloalkylphenyl, alkylbenzoate, alkoxyphenyl, or alkylphenyl sulphone, the haloalkyl or alkyl group comprises from 1 to 4 carbon atoms, for example 1 or 2 carbon atoms, and/or when R₁ is heterocyclyl, the heterocyclyl contains from 3 to 6 carbon atoms and 1 or 2 heteroatoms (e.g. oxygen or sulphur), for example, from 4 or 5 carbon atoms and 1 heteroatom (e.g. oxygen or sulphur), for example wherein the heterocyclyl is furan or thiophene.

In certain embodiments, R₁ is phenyl, fluorophenyl, trifluoromethylphenyl, methoxyphenyl, methylphenyl sulphone, or cyclopropyl and R₂ is phenyl, trifluoromethylphenyl, methyl benzoate, methoxyphenyl, cyclopropyl, or ethenyl. In certain embodiments, R₁ is phenyl, fluorophenyl, trifluoromethylphenyl, methoxyphenyl, or methylphenyl sulphone, and R₂ is phenyl, trifluoromethylphenyl, methylbenzoate, methoxyphenyl, or ethenyl. In certain embodiments, R₁ is phenyl or trifluoromethylphenyl and R₂ is phenyl, trifluoromethylphenyl, methylbenzoate, methoxyphenyl, or ethenyl.

In certain embodiments, R₁ is phenyl, fluorophenyl, trifluoromethylphenyl, methoxyphenyl, methylphenyl sulphone, cyclopropyl, furan or thiophene and R₂ is phenyl, trifluoromethylphenyl, methylbenzoate, methoxyphenyl, cyclopropyl, or ethenyl. In certain embodiments, R₁ is phenyl, fluorophenyl, trifluoromethylphenyl, methoxyphenyl, methylphenyl sulphone, furan or thiophene and R₂ is phenyl, trifluoromethylphenyl, methylbenzoate, methoxyphenyl, or ethenyl. In certain embodiments, R₁ is phenyl, trifluoromethylphenyl, furan or thiophene and R₂ is phenyl, trifluoromethylphenyl, methyl benzoate, methoxyphenyl, or ethenyl.

The carbon-carbon double bond between the sulphone and disulphide groups of the compound of formula (I) may have E or Z stereochemistry. Thus, formula (I) encompasses both E and Z stereoisomers.

In certain embodiments, the process for making the compound of formula (I) is stereospecific such that one stereoisomer is preferentially formed over the other, for example such that only one stereoisomer is formed. In certain embodiments, the E and/or Z stereoisomers may be separated from a mixture of E and Z isomers. Thus, in certain embodiments, the compound of formula (I) has E configuration. In alternative embodiments, the compound of formula (I) has Z configuration.

In certain embodiments, the process for making the compound of formula (I) produces a mixture of stereoisomers, for example mixture containing approximately equal amounts of E and Z stereo isomers (e.g. from about 10:90 to about 90:10 or from about 30:70 to about 70:30 or from about 40:60 to about 60:40 or from about 45:55 to about 55:45 or about 50:50 E:Z). Thus, the pharmaceutical compositions described herein may, for example, comprise a mixture of E and Z stereoisomers of formula (I).

In certain embodiments, the compound of formula (I) is one of the following compounds. These compounds may have E configuration or Z configuration. Compositions and pharmaceutical compositions comprising one of the following compounds may, for example, comprise a mixture of E stereoisomers and Z stereoisomers of that compound.

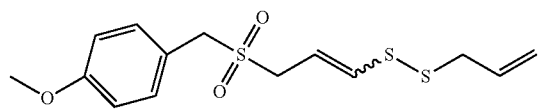 [SMILES: C=CCSSC=CCS(=O)(=O)Cc1ccc(OC)cc1]

1-methoxy-4-{[3-(prop-2-en-1-yldisulfanyl)prop-2-ene-1-sulfonyl]methyl}benzene

NMR: δ_H (400 MHz, CDCl₃) 7.32-7.27 (2H, m), 6.93-6.88 (2H, m), Z-isomer: 6.56 (0.77H, dt, J=9.5, 1.1 Hz), E-isomer: 6.33 (0.23H, br t, J=14.8 Hz), 5.93-5.74 (1.23H, m), Z-isomer: 5.69 (0.77H, dt, J=9.5, 7.7 Hz), 5.21-5.12 (2H, m), 4.13 (2H, s), E-isomer: 3.80 (s) overlapping Z-isomer: 3.80 (s) (total 3H), Z-isomer: 3.72 (1.54H, br d, J=8.2), E-isomer: 3.59 (0.46H, d, J=7.6 Hz).

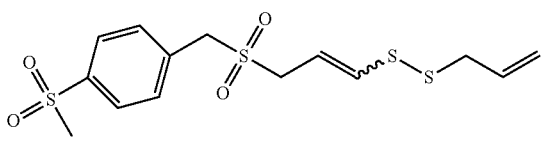 [SMILES: C=CCSSC=CCS(=O)(=O)Cc1ccc(S(C)(=O)=O)cc1]

1-methanesulfonyl-4-{[3-(prop-2-en-1-yldisulfanyl)prop-2-ene-1-sulfonyl]methyl}benzene NMR: δH (400 MHz, CDCl₃) 7.99-7.94 (2H, m), 7.63-7.58 (2H, m), Z-isomer: 6.62 (0.66H, doublet of unresolved triplets, J=9.5 Hz), E-isomer: 6.41 (0.34H, br d, J=14.8 Hz), E-isomer: 5.90 (0.34H, dt, J=14.8 Hz) 5.87-5.75 (1H, m) overlapping Z-isomer: 5.73 (0.66H, dt, J=9.5, 7.8 Hz), 5.21-5.13 (2H, m), 4.26 (2H, s), Z-isomer: 3.84 (1.32H, br d, J=8.4 Hz), E-isomer: 3.72 (0.68H, br d, J=7.9 Hz), Z-isomer: 3.38 (1.32H, br d, J=7.4 Hz) overlapping E-isomer: 3.35 (0.68H, br d, J=7.4 Hz), E-isomer: 3.06 (s) overlapping Z-isomer: 3.05 (s) (total 3H).

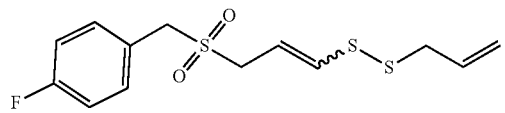 [SMILES: C=CCSSC=CCS(=O)(=O)Cc1ccc(F)cc1]

1-fluoro-4-{[3-(prop-2-en-1-yldisulfanyl)prop-2-ene-1-sulfonyl]methyl}benzene

NMR: δH (400 MHz, CDCl₃) 7.40-7.33 (2H, m), 7.13-7.04 (2H, m), Z-isomer: 6.58 (0.71H, dt, J=9.5, 1.1 Hz), E-isomer: 6.35 (0.29H, doublet of unresolved triplets, J=14.8 Hz), E-isomer: 5.89 (dt, J=14.8, 7.6 Hz) overlapping 5.86-7.74 (m) total (1.29H), Z-isomer: 5.70 (0.71H, dt, J=9.5, 7.7 Hz), 5.21-5.12 (2H, m), 4.15 (2H, s), Z-isomer:

3.76 (1.42H, br d, J=7.7 Hz), E-isomer: 3.62 (0.58H, br d, J=7.6 Hz), 3.38-3.33 (2H, m).

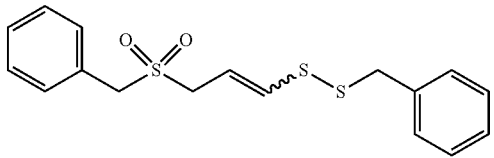 [SMILES: O=S(=O)(CC=CSSCc1ccccc1)Cc1ccccc1]

{[(3-phenylmethanesulfonylprop-1-en-1-yl)disulfanyl]methyl}benzene

NMR: δH (400 MHz, CDCl₃) 7.42-7.21 (10H, m) overlapping residual CHCl₃ signal, Z-isomer: 6.21 (0.68H, dt, J=9.5, 1.1 Hz), E-isomer: 6.12 (0.32H, doublet of unresolved triplets, J=14.8 Hz), E-isomer: 5.78 (0.32H, dt, J=14.9, 7.6 Hz), Z-isomer: 5.55 (0.68H, dt, J=9.5, 7.7 Hz), Z-isomer: 4.14 (1.36H, s), E-isomer: 4.13 (0.64H, s), Z-isomer: 3.92 (1.36H, s), E-isomer: 3.91 (0.64H, s), Z-isomer: 3.67 (1.36H, d, J=7.8 Hz), E-isomer: 3.49 (0.64H, d, J=7.6 Hz).

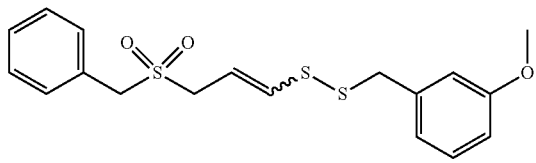 [SMILES: COc1cccc(CSSC=CCS(=O)(=O)Cc2ccccc2)c1]

1-methoxy-3-{[(3-phenylmethanesulfonylprop-1-en-1-yl)disulfanyl]methyl}benzene

NMR: δH (400 MHz, CDCl3) 7.42-7.33 (5H, m), 7.28-7.15 (2H, m), 6.89-6.83 (2H, m), Z-isomer: 6.26 (0.7H, doublet of unresolved triplets, J=9.5 Hz), E-isomer: 6.15 (0.3H, doublet of unresolved triplets, J=14.8 Hz), E-isomer: 5.82 (0.3H, dt, J=14.8, 7.6 Hz), Z-isomer: 5.56 (0.7H, dt, J=9.54, 7.70 Hz), Z-isomer: 4.15 (1.4H, s), E-isomer: 4.12 (0.6H, s), Z-isomer: 3.97 (1.4H, s), E-isomer: 3.95 (0.6H, s), E-isomer: 3.86 (0.9H, s), Z-isomer: 3.83 (2.1H, s), Z-isomer: 3.69 (1.4H, d, J=8.2 Hz), E-isomer 3.49 (0.6H, d, J=7.6 Hz).

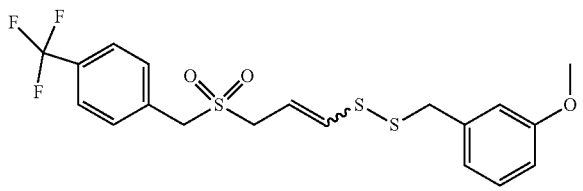 [SMILES: COc1cccc(CSSC=CCS(=O)(=O)Cc2ccc(C(F)(F)F)cc2)c1]

1-methoxy-3-({[-3-{[4-(trifluoromethyl)phenyl]methanesulfonyl}prop-1-en-1-yl]disulfanyl}methyl)benzene NMR: ¹H-nmr (600 Hz, CDCl₃): 3.77 (d, J=7.8 Hz, 2H, CH₂—CH=), 3.81 (s, 3H, OCH₃), 3.95 (s, 2H, CH₂—S—S), 4.22 (s, 2H, CH₂SO₂), 5.60-5.65 (m, 1H, CH₂—CH=), 6.31 (d, J=9.6 Hz, 2H, =CH—S—S), 6.85 (d, J=7.2 Hz, 1H, CH—Ar), 6.91 (d, J=7.2 Hz, 1H, CH—Ar), 7.25 (t, J=7.8 Hz, 2H, CH—Ar), 7.54 (d, J=7.8 Hz, 2H, CH—Ar), 7.69 (d, J=7.8 Hz, 2H, CH—Ar).

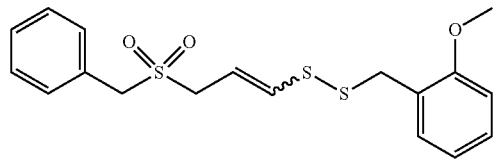 [SMILES: COc1ccccc1CSSC=CCS(=O)(=O)Cc1ccccc1]

1-methoxy-2-{[(3-phenylmethanesulfonylprop-1-en-1-yl)disulfanyl]methyl}benzene

NMR: δH (400 MHz, CDCl3) 7.42-7.33 (5H, m), 7.28-7.15 (2H, m), 6.89-6.83 (2H, m), Z-isomer: 6.26 (0.7H, doublet of unresolved triplets, J=9.5 Hz), E-isomer: 6.15 (0.3H, doublet of unresolved triplets, J=14.8 Hz), E-isomer: 5.82 (0.3H, dt, J=14.8, 7.6 Hz), Z-isomer: 5.56 (0.7H, dt, J=9.54, 7.70 Hz), Z-isomer: 4.15 (1.4H, s), E-isomer: 4.12 (0.6H, s), Z-isomer: 3.97 (1.4H, s), E-isomer: 3.95 (0.6H, s), E-isomer: 3.86 (0.9H, s), Z-isomer: 3.83 (2.1H, s), Z-isomer: 3.69 (1.4H, d, J=8.2 Hz), E-isomer 3.49 (0.6H, d, J=7.6 Hz).

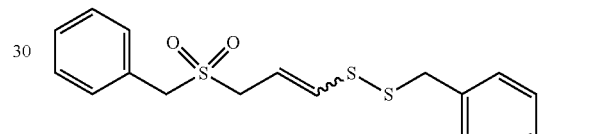

1-methoxy-4-{[(3-phenylmethanesulfonylprop-1-en-1-yl)disulfanyl]methyl}benzene

NMR: δH (400 MHz, CDCl3) 7.41-7.33 (5H, m), 7.24-7.16 (2H, m), 6.85-6.79 (2H, m), Z-isomer: 6.25 (0.6H, dt, J=9.5, 1.1 Hz), E-isomer: (0.4H, doublet of unresolved triplets, J=14.9 Hz), E-isomer: 5.79 (0.4H, dt, J=14.8, 7.7 Hz), Z-isomer: 5.58 (0.6H, dt, J=9.5, 7.7 Hz), Z-isomer: 4.15 (1.2H, s), E-isomer: 4.13 (0.8H, s), Z-isomer: 3.89 (1.2H, s), E-isomer: 3.87 (0.8H, s), Z-isomer: 3.77 (1.8H, s), E-isomer: 3.74 (1.2H, s), Z-isomer 3.69 (1.2H, d, J=8.2 Hz), E-isomer: 3.51 (0.8H, d, J=7.6 Hz).

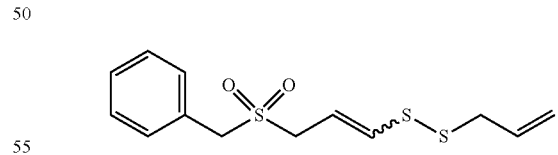

{[3-(prop-2-en-1-yldisulfanyl)prop-2-ene-1-sulfonyl]methyl}benzene

NMR: δH (400 MHz, CDCl3) 7.40-7.38 (5H, m), Z-isomer: 6.57 (0.72H, dt, J=9.5, 1.1 Hz), E-isomer: 6.34 (0.28H doublet of unresolved triplets, J=14.9 Hz), E-isomer: 5.88 (0.28H, dt, J=14.8, 7.7 Hz) overlapping 5.85-5.74 (1H, m), Z-isomer: 5.70 (0.72H, dt, J=9.5, 7.7 Hz), 5.22-5.12 (2H, m), 4.19 (2H, s), E-isomer: 3.74 (1.54H, dd, J=7.7, 0.5 Hz), Z-isomer: 3.60 (0.54H, d, 7.6 Hz), 3.38-3.33 (2H, m).

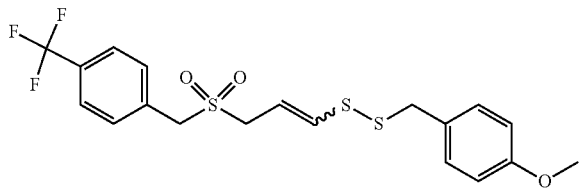 [SMILES: COc1ccc(CSSC=CCS(=O)(=O)Cc2ccc(C(F)(F)F)cc2)cc1]

1-methoxy-4-({[-3-{[4-(trifluoromethyl)phenyl]methanesulfonyl}prop-1-en-1-yl]disulfanyl}methyl)benzene NMR: ¹H-nmr (600 Hz, CDCl₃): 3.59 (d, J=7.8 Hz, 2H, CH₂—SO₂), 3.78 (s, 3H, OCH₃), 3.92 (s, 2H, CH₂—S—S), 4.20 (s, 2H, CH₂—C—Ar), 5.78-5.88 (m, 1H, CH=), 6.21 (d, J=15 Hz, 1H, CH—S—S), 6.87 (d, J=8.4 Hz, 2H, CH—Ar), 7.26 (d, J=8.4 Hz, 2H, CH—Ar), 7.53 (d, J=7.8 Hz, 2H, CH—Ar), 7.70 (d, J=7.8 Hz, 2H, CH—Ar).

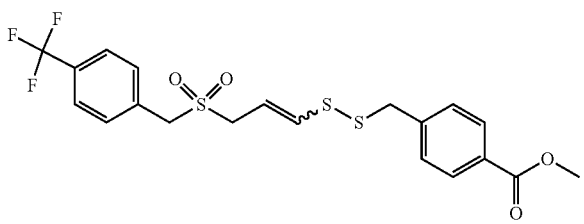 [SMILES: COC(=O)c1ccc(CSSC=CCS(=O)(=O)Cc2ccc(C(F)(F)F)cc2)cc1]

Methyl-4-({[-3-{[4-(trifluoromethyl)phenyl]methanesulfonyl}prop-1-en-1-yl]disulfanyl}methyl)benzoate NMR: δH (400 MHz, CDCl₃) 7.97 (2H, AA'BB'), 7.68-7.61 (2H, m), 7.52-7.45 (2H, m), 7.39-7.32 (2H, m), 6.14 (0.16H, dt, J=14.9, 1.1 Hz), 5.77 (0.16H, dt, J=14.9, 7.7 Hz), 4.15 (0.32H, s), 3.93 (0.32H, s), 3.86 (0.48H, s), 3.53 (0.32H, d, J=7.5 Hz).

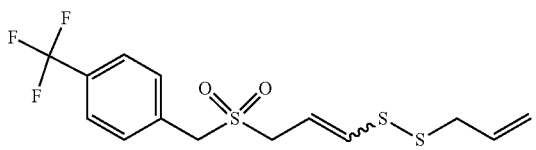 [SMILES: C=CCSSC=CCS(=O)(=O)Cc1ccc(C(F)(F)F)cc1]

1-{[-3-(prop-2-en-1-yldisulfanyl)prop-2-ene-1-sulfonyl]methyl}-4-(trifluoromethyl)benzene NMR: ¹H-nmr (600 Hz, CDCl₃): 3.39 (d, J=7.2 Hz, 2H, CH₂—S—S), 3.70 (d, J=7.8 Hz, 2H, CH₂—CH=), 4.28 (s, 2H, CH₂), 5.22 (dd, J=9, 15 Hz, 2H, CH₂=), 5.86-5.96 (m, 2H, —CH=), 6.42 (d, J=15 Hz, 1H, =CHS-S), 7.57 (d, J=7.8 Hz, 2H, CH—Ar), 7.71 (d, J=7.8 Hz, 2H, CH—Ar).

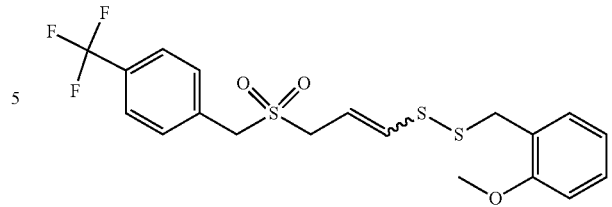

1-methoxy-2-{[(3-{[4-(trifluoromethyl)phenyl]methanesulfonyl}prop-1-en-1-yl)disulfanyl]methyl}benzene NMR: δH (400 MHz, CDCl3) 7.64 (2H, d, J=8.1 Hz), 7.52-7.46 (2H, m), 7.29-7.15 (2H, m) overlapping CHCl3 signal, 6.89-6.83 (2H, m), Z-isomer: 6.27 (0.58H, dt, J=8.4, 1.1 Hz), E-isomer: 6.17 (0.42H, dt, J=14.8, 1.1 Hz), E-isomer: 5.82 (0.42H, dt, J=14.8, 7.6 Hz), Z-isomer: 5.57 (0.58H, dt, J=9.5, 7.8 Hz), Z-isomer: 4.18 (1.16H, s), E-isomer: 4.14 (0.84H, s), Z-isomer: 3.98 (1.16H, s), E-isomer: 3.96 (0.84H, s), E-isomer: 3.86 (1.26H, s), Z-isomer: 3.83 (1.74H, s), Z-isomer: 3.74 (1.16H, dd, J=7.8, 0.7 Hz), E-isomer: 3.53 (0.84H, d, J=7.5 Hz).

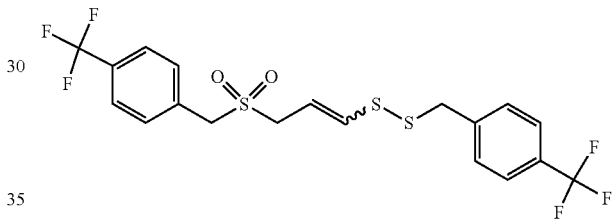

1-(trifluoromethyl)-4-{[(3-{[4-(trifluoromethyl)phenyl]methanesulfonyl}prop-1-en-1-yl)disulfanyl]methyl}benzene NMR: δH (400 MHz, CDCl3) 7.68-7.62 (2H, m), 7.56 (2H, d, J=8.0 Hz), 7.49 (2H, d, J=8.1 Hz), 7.43-7.37 (2H, m), Z-isomer: 6.25 (0.72H, d, J=9.5 Hz), E-isomer: 6.13 (0.28H, d, J=14.9 Hz), E-isomer: 5.75 (0.28H, dt, J=14.9, 7.5 Hz), Z-isomer: 5.58 (0.72H, dt, J=9.5, 7.8 Hz), 4.19 (2H, s), Z-isomer: 3.96 (1.44H, s), Z-isomer: 3.92 (0.56H, s), Z-isomer: 3.70 (1.44H, d, J=7.9 Hz), E-isomer: 3.52 (0.56H, d, J=7.7 Hz).

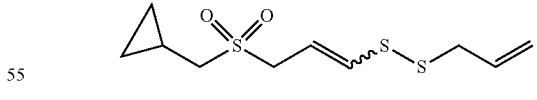

{[3-(prop-2-en-1-yldisulfanyl)prop-2-ene-1-sulfonyl]methyl}cyclopropane

NMR: δH (400 MHz, CDCl3) Z-isomer: 6.56 (0.58H, dt, J=9.5, 1.2 Hz), E-isomer: 6.40 (0.42H, dt, J=14.8, 1.0 Hz), E-isomer: 5.92 (0.42H, dt, J=14.9, 7.6 Hz), 5.87-5.75 (1H, m) overlapping Z-isomer: 5.72 (0.58H, dt, J=9.5, 7.8 Hz), 5.21-5.13 (2H, m), Z-isomer: 3.88 (1.16H, d, J=7.8 Hz), E-isomer: 3.79 (0.84H, d, J=7.6 Hz), Z-isomer: 3.37 (1.16H, d, J=7.3), overlapping E-isomer: 3.34 (0.84H, d, J=7.4 Hz), Z-isomer: 2.87 (1.16H, d, J=7.2 Hz) overlapping E-isomer: 2.87 (0.84H, d, J=7.2 Hz), 1.23-1.10 (1H, m), 0.79-0.72 (2H, m), 0.43-0.35 (2H, m).

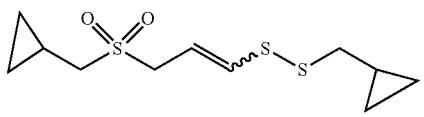 [SMILES: O=S(=O)(CC=CSSCC1CC1)CC1CC1]

{[(3-cyclopropylmethanesulfonylprop-1-en-1-yl)disulfanyl]methyl}cyclopropane

NMR: δH (400 MHz, CDCl3) Z-isomer: 6.65 (0.62H, dt, J=9.5, 1.1 Hz), E-isomer: 6.47 (0.38H, dt, J=14.8, 1.1 Hz), E-isomer: 5.96 (0.38H, dt, J=14.8, 7.7 Hz), Z-isomer: 5.72 (0.62H, dt, J=9.5, 7.8 Hz), Z-isomer: 3.88 (1.24H, d, J=7.7 Hz), E-isomer: 3.80 (0.76H, d, J=7.6 Hz), 2.90-2.84 (2H, overlapping doublets), Z-isomer: 2.70 (1.24H, d, J=7.2 Hz), E-isomer: 2.67 (0.76H, d, J=7.2 Hz), 1.23-1.00 (2H, m), 0.78-0.72 (2H, m), 0.64-0.57 (2H, m), 0.43-0.35 (2H, m), 0.30-0.24 (2H, m).

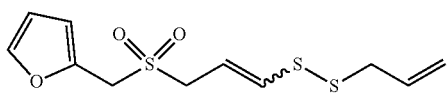 [SMILES: C=CCSSC=CCS(=O)(=O)Cc1ccco1]

2-{[prop-2-en-1-yldisulfanyl)prop-2-ene-1-sulfonyl]methyl}furan

NMR: δH (400 MHz, CDCl$_3$): 7.41-7.42 (1H, m), 6.55 (0.64H, dt, J=9.5, 1.1 Hz), 6.48 (0.64H, dd, J=3.3, 0.7 Hz), 6.47 (0.34 Hz, dd, J=3.4, 0.6 Hz), 6.36-6.40 (1.34H, m), 5.64 (0.66H, dt, J=9.5, 7.7 Hz), 5.08-5.16 (2H, m), 4.23 (d, 2H, J=7.5 Hz), 3.79 (1.28H, d, J=7.8 Hz), 3.64 (0.68H, d, J=7.8 Hz), 3.32. 3.30 (4H, pair of unresolved doublets).

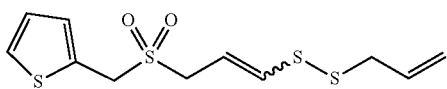 [SMILES: C=CCSSC=CCS(=O)(=O)Cc1cccs1]

2-{[3-(prop-2-en-1-yldisulfanyl)prop-2-ene-1-sulfonyl]methyl}thiophene

NMR: δH (400 MHz, CDCl$_3$): 7.37 (1H, dd, J=5.2, 1.2 Hz), 7.14-7.18 (1H m), 7.05 (1H, dt, J=5.2, 3.6 Hz), 6.58 (0.56H, dt, J=9.5, 1.1 Hz), 6.39 (0.34H, dt, J=14.8, 0.5 Hz), 5.95-5.74 (1.34H, m), 5.68 (0.56H, dt, J=9.5, 7.8 Hz), 5.19 (0.68H, dq, J=8.9, 1.3 Hz), 5.15 (1.32H, dt, J=8.7, 0.9 Hz), 4.40 (2H, d, J=5.4 Hz), 3.80 (1H, d, J=7.8 Hz), 3.36 (1.22H, d, J=7.3 Hz), 3.34 (0.68H, d, J=7.4 Hz).

In certain embodiments, the compound of formula (I) is one of the following compounds with E configuration (compound according to formula (IA)).

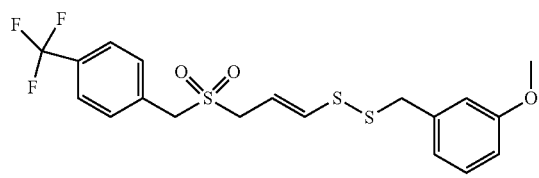

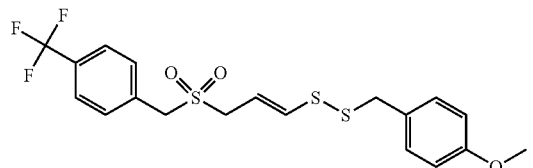

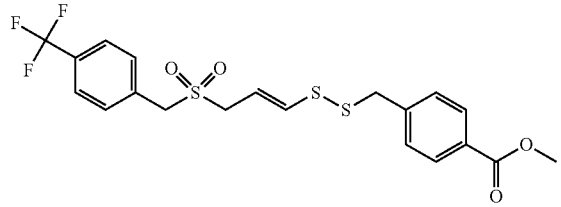

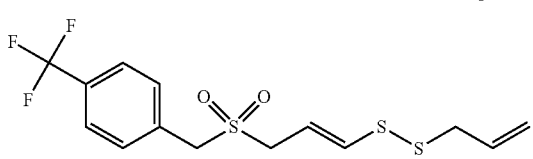

In certain embodiments, the compound of formula (I) is one of the following compounds with Z configuration (compound according to formula (IB)).

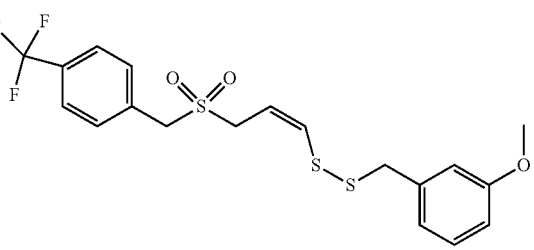

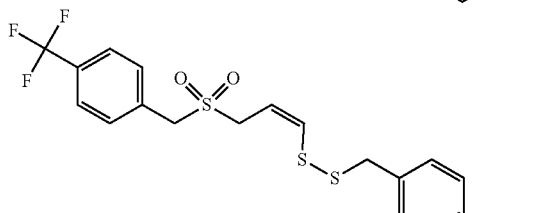

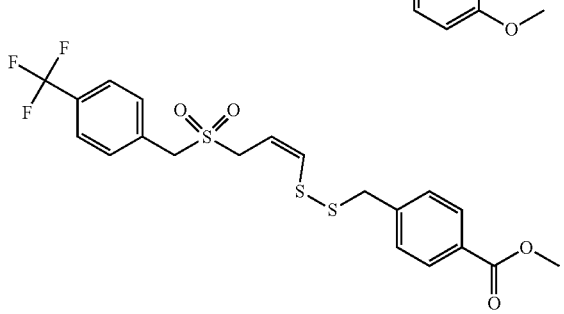

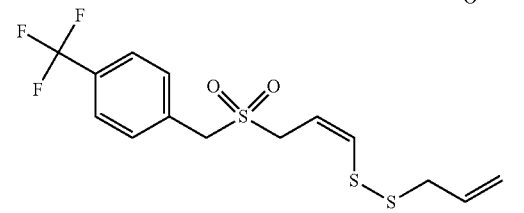

In certain embodiments, the compound of formula (I) is

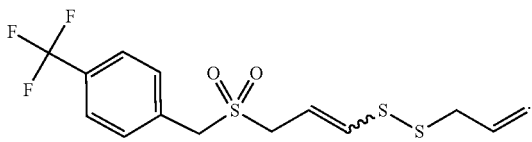

This compound may have E configuration or Z configuration. Compositions or pharmaceutical compositions comprising this compound may, for example, comprise a mixture of E and Z stereoisomers of this compound.

There is further provided herein a pharmaceutical composition comprising a compound of formula (I) and a pharmaceutically acceptable carrier and/or excipient and/or diluent. The term "pharmaceutical composition" or "medicament" in the context of this invention means a composition comprising (a pharmaceutically effective amount of) a compound of formula (I) and additionally one or more pharmaceutically acceptable carriers and/or excipients and/or diluents.

The pharmaceutical composition may further contain ingredients selected from, for example, adjuvants, vehicles, preserving agents, fillers, binders, disintegrating agents, wetting agents, emulsifying agents, suspending agents, sweetening agents, flavouring agents, perfuming agents, lubricating agents, coating agents, encapsulating agents, aerosolising agents, and dispersing agents, depending on the nature of the mode of administration and dosage forms.

The pharmaceutical compositions may take the form, for example, of solid preparations including tablets, capsules, caplets, drageés, lozenges, granules, powders, pellets, beads, dressings, bandages, patches, surgical patches, catheters, pastes, and cachets; semi-solid preparations including gels, balms, creams, ointments, gums, foams, liniments, glues, and lotions; and liquid preparations including elixirs, syrups, suspensions, sprays, emulsions, lotions, soaps, shakes, collodions, paints, lavages, irrigates, and solutions; aerosol preparations using solutions, water based systems, suspensions, or dispersion systems, foam systems, and/or utilizing liquefied gas propellants, compressed gases, dry powder, and nebulisation. Techniques and formulations generally may be found in Remington, The Science and Practice of Pharmacy, Mack Publishing Co., Easton, PA, latest edition.

The pharmaceutical composition (medicament) may, for example, be suitable for oral, nasal, topical, suppository, intravenous or intradermal administration. The composition may alternatively be a nutraceutical composition, for example, a foodstuff, food supplement, dietary supplement, health supplement, meal replacement product, beverage, beverage supplement, food additive, animal feed or feed additive.

The compound of formula (I) may, for example, be administered in combination with one or more other biologically active agents. Thus, the pharmaceutical composition may comprise one or more other biologically active agents. The one or more biologically active agents may, for example, be selected from debridement agents; soaps; antibiotic agents such as penicillins (e.g. penicillin, amoxicillin), cephalosporins (e.g. cephalexin), macrolides (e.g. erythromycin, clarithromycin, azithromycin), fluoroquinolones (e.g. ciprofloxacin, levoflacin, ofloxacin), sulphonamides (e.g. co-trimoxazole, trimethoprim), tetracyclines (e.g. tetracycline, doxycycline) and aminoglycosides (e.g. gentamicin, tobramycin); antiseptic agents such as taurolidine, potassium permanganate, boric acid, surfactants (e.g. octenidine dihydrochloride, octenidine dihydrochloride/phenoxyethanol), alcohols (e.g. ethanol, isopropyl alcohol, n-propanol), anilides (e.g. tridocarban), biguanides (e.g. chlorhexidine, polyhexadine, polyhexamethylene, polyhexanide), bisphenols (e.g. diphenyl ether-triclosan, chlorinated phenol-hexachlorophene), chlorine compounds (e.g. sodium hypochlorite), halophenols (e.g. chloroxylenol), iodine compounds (e.g. Lugol's solution, tincture of iodine, iodophores including polyvinylpyrrolidone iodine, povidone-iodine, cadexomer-iodine), silver compounds (e.g. silver sulphadiazine, silver nitrate, (irrespective of source i.e. silver released from solutions, creams ointments or nanocrystalline silver), peroxygens (e.g. hydrogen peroxide), and oxygen treatments (in the form of radical oxygen species and gaseous $O_2$ (e.g. hyperbaric chambers, Nitrox/Natrox); anti-inflammatory agents (e.g. nonsteroidal anti-inflammatory drugs (NSAIDs) such as aspirin, ibuprofen, and naproxen), anti-thrombotic agents such as anticoagulants (e.g. heparin or warfarin), antiplatelet drugs (e.g. aspirin), and thrombolytic drugs (e.g. streptokinase); antimicrobial light sources, wound healing devices, and photodynamic therapy sources within the ultraviolet, visible, violet, blue, green, yellow, red and infrared regions (singularly or a combination thereof), such as deep penetrating light therapy, low level light/laser therapy, utilizing light from such sources as lasers, wide or short range polarized and unpolarized light and incoherent light sources e.g. light emitting diodes (LED's).

The compound of formula (I) may, for example, be administered in combination with one or more other biologically active agents used for treating cystic fibrosis. Thus, the pharmaceutical composition may comprise one or more other biologically active agents used for treating cystic fibrosis. Examples of biologically active agents used for treating cystic fibrosis include, for example, modulators of cystic fibrosis transmembrane conductance regulators (CFTR) (e.g. ivacaftors, lumacaftor, tezacaftor), antibiotics, mucolytics (e.g. dornase alfa, hypertonic sodium chloride, mannitol), immunomodulatory drugs (e.g. azithromycin), bronchodilators, and steroid medicines.

In certain embodiments, the one or more other biologically active agent or agents are present in the composition or pharmaceutical composition in an amount ranging from about 0.00001 wt. % to about 99 wt. %, based on the total weight of the composition, for example, about 0.0001 wt. % to about 80 wt. %, or about 0.001 wt. % to about 50 wt. %, or about 0.1 wt. % to about 15 wt. %, or from about 0.5 wt. % to about 10 wt. %, or from about 0.5 wt. % to about 5 wt. %, or from about 0.1 wt. % to about 3 wt. %, or from about 0.1 wt. % to about 2 wt. %, or from about 0.1 wt. % to about 1 wt. %, or from about 0.001 wt. % to about 5 wt. %, or from about 0.001 wt. % to about 2 wt. %, or from about 0.001 wt. % to about 1 wt. %, or from about 0.001 wt. % to 20 about 0.5 wt. %, or from about 0.001 wt. % to about 0.1 wt. %, or from about 0.001 wt. % to about 0.01 wt. %.

In solid dosage forms for oral administration, the compound of formula (I) may be mixed with one or more pharmaceutically acceptable carriers, such as dicalcium phosphate or macrolides, and/or any of the following: diluents, fillers or extenders, such as, for example, starches, silicon lactose, sucrose, glucose, mannitol, microcrystalline cellulose and/or silicic acid; binders, such as, for example, hydroxypropylcellulose, hypromellose, hydroxypropyl methylcellulose, carboxymethylcellulose, gelatine, polyvinyl pyrrolidones, polyvinyl acetate, sucrose and/or acacia; disintegrating agents, such as starch, for example, potato or tapioca starch, starch derivatives such as sodium starch glycolate, crospolyvinylpyrollidone, calcium carbonate, croscarmellose sodium, alginic acid, and certain silicates; lubricants, such as talc, calcium stearate, magnesium stearate, stearic acid, sodium sulfate stearyl fumarate, solid polyethylene glycols, solubilisers such as sodium lauryl sulfate, ammonium dodecyl sulfate and sodium dodecyl sulfate; surfactants such as non-ionic surfactants, for example, polyglycerol alkyl ethers, glucosyl dialkyl ethers, crownethers; ester-linked surfactants, for example, polyoxyethylene alkyl ethers, Brij, Spans (sorbitan esters) and Tweens (Polysorbates); anionic surfactants, for example, sulfonate, phosphate, sulfate and carboxylates; alkyl carboxylates (soaps), for example, sodium stearate, dioctyl sodium sulfosuccinate, perfluorooctanesulfonate, linear alkylbenzene sulfonates (LABs) and perfluorobutanesulfonate; alkyl-aryl ether phosphates, sodium lauroyl sarcosinate and carboxylate-based fluorosurfactants, for example, perfluorononanoate and perfluorooctanoate; cationic surfactants, for example, benzalkonium chloride, cetylpyridinium chloride, and benzethonium chloride; alkyltrimethylammonium salts, for example, cetyl trimethylammonium bromide (CTAB) and cetyl trimethylammonium chloride (CTAC); zwitterionic surfactants, for example, sulfonates, as in the sultaines CHAPS (3-[(3-Cholamidopropyl)dimethylammonio]-1-propanesulfonate); betaines, for example, cocamidopropyl betadine; flavouring and colouring agents and mixtures thereof.

Tablets, and other solid dosage forms of the pharmaceutical compositions, may optionally be prepared with coatings and shells, such as enteric coatings and other coatings well known in the pharmaceutical-formulation art. They may also be formulated so as to provide slow or controlled release of the active ingredient(s) therein using, for example, natural and synthetic polymers such as hydroxypropylmethyl cellulose methacrylates, methacrylic acid copolymers (e.g. methyl acrylate-methacrylic acid copolymers and methyl methacrylate-methacrylic acid copolymers), shellac, ethylcellulose, cellulose acetate phthalate, cellulose acetate trimellitate, polyvinyl acetate phthalate, cellulose acetate succinate, hydroxyl propyl methyl cellulose acetate succinate, sodium alginate, waxes, fatty acids, zein, respectively, in varying proportions to provide the desired release profile, other polymer matrices, liposomes and/or microspheres may also be used. These compositions may also optionally contain colourants and/or opacifying agents and may be of a composition such that they release the active ingredient(s) only, or preferentially, in a certain portion of the gastrointestinal tract, optionally, in a delayed manner.

The pharmaceutical compositions may comprise no more than about 50% w/w of pharmaceutically acceptable carrier and/or excipient and/or diluent, for example, no more than about 45% w/w of pharmaceutically acceptable carrier and/or excipients and/or diluents, or no more than about 40% of w/w pharmaceutically acceptable carrier and/or excipients and/or diluents, or no more than about 35% w/w of pharmaceutically acceptable carrier and/or excipients and/or diluents. For example, the pharmaceutical composition may comprise at least about 1% w/w, or at least about 10% w/w, or at least about 15% w/w, or at least about 20% w/w, or at least about 25% w/w, or at least about 30% w/w of pharmaceutically acceptable carrier and/or excipients and/or diluents.

Liquid form preparations include solutions, suspensions, and emulsions, for example, water or water-propylene glycol solutions for oral administration. Liquid preparations can also be formulated in solution in aqueous polyethylene glycol solution. In certain embodiments, the compound of formula (I) may be mixed with one or more pharmaceutically acceptable carriers, such as water and/or any of the following: solvent such as propylene glycol, alcohol; humectant such as glycerol; sweeteners such as liquid glucose, corn syrup and sucrose; artificial sweeteners such as aspartame, stevia and sucralose; preservatives such as benzoates and parabens; viscosity modifiers/thickeners such as gums and alginates; buffering agents; flavouring agents and colouring agents.

Also included are solid form preparations, for example, tablets, capsules, granules and powder, which are intended to be converted, shortly before use, to liquid form preparations for oral administration. Such liquid forms include solutions, suspensions, and emulsions. These particular solid form preparations are most conveniently provided in unit dose form and as such are used to provide a single liquid dosage unit. Alternatively, sufficient solid may be provided so that multiple individual liquid doses may be reconstituted when required, by measuring predetermined volumes of the solid form preparation as with a spoon, or other measuring device. The solid form preparations intended to be converted to liquid form may contain, in addition to the active material, flavourings, colourants, stabilizers, buffers, artificial and natural sweeteners, dispersants, thickeners, solubilising agents, and the like. The liquid utilized for preparing the liquid form preparation may be water, isotonic water, juices, milk, ethanol, and the like as well as mixtures thereof.

The components referred to hereinbefore and hereinafter are in particular selected from among those such as are listed in pharmacopoeia, e.g. in the US Pharmacopoeia National Formulary, the Pharmacopoea Europea, the Pharmacopoea Helvetica, the British Pharmacopoeia, the German Pharmacopoeia, the Chinese Pharmacopoeia, the Japanese Pharmacopoeia, or supplements, such as by way of decrees.

Uses of the Compounds of Formula (I) and Pharmaceutical Compositions

The compounds and pharmaceutical compositions described herein may be used in various therapeutic and non-therapeutic applications. For example, the compounds and pharmaceutical compositions described herein may be used to provide one or more beneficial effects to a patient. For example, the compounds and pharmaceutical compositions described herein may be used in various cosmetic applications. For example, the compounds and pharmaceutical compositions described herein may be used in an in vitro method or in an in vivo method. The methods may comprise administering the compound or pharmaceutical composition described herein to a subject.

The term "therapeutic treatment" or "therapeutic method", also includes prophylaxis and the alleviation of symptoms of a disease and/or disorder in a subject, although not cosmetic treatments.

The expression "treating or preventing" and analogous terms used herein refers to all forms of healthcare intended to remove or avoid the disease and/or disorder or to relieve its symptoms, including preventive and curative care, as judged according to any of the tests available according to the prevailing medical practice. An intervention that aims with reasonable expectation to achieve a particular result but does not always do so is included within the expression "treating or preventing". An intervention that succeeds in slowing or halting progression of a disease and/or disorder is included within the expression "treating or preventing".

In certain embodiments, the subject is a human. In other embodiments, the subject is a mammal other than a human, such as non-human primates (e.g. apes, monkeys and lemurs), companion animals such as cats or dogs, working and sporting animals such as dogs, horses and ponies, farm animals such as pigs, sheep, goats, deer, oxen and cattle, and laboratory animals such as rodents (e.g. rabbits, rats, mice, hamsters, gerbils or guinea pigs).

The amount of compounds or pharmaceutical composition administered may be varied depending upon the requirements of the subject or use. For both therapeutic and non-therapeutic applications, the amount of compound or pharmaceutical composition administered may be varied depending upon the desired results, the requirements of the subject and the severity of the condition being treated. Determination of the proper amount/dosage for a particular situation is within the skill of the art. For example, for therapeutic applications a physician or veterinarian having ordinary skill in the art can readily determine and prescribe the effective amount of the compound or pharmaceutical composition required. The total daily amount/dosage may be divided and administered in portions during the day if desired.

In general, a suitable daily dose of active agents (i.e. compounds of formula (I)) will be that amount which is the lowest dose effective to produce the desired effect, for example, a therapeutic effect. It is contemplated that a wide range of doses may be used, due to the non-toxic nature of the composition. A person of ordinary skill in the art will understand that a suitable dose or dosage will typically vary from subject to subject, and will dependent on factors such as the severity of health conditions of the subject at the outset of administration. For example, the dose of active agents in the composition may be up to 15 g per day, for example, up to about 10 g per day, or up to about 5 g per day.

In certain embodiments, the doses of active agents is in the range of 100 mg to about 3 g per day, which may be administered as two or three or more sub-doses administered separately at appropriate intervals throughout the day, optionally in unit dosage forms. In certain embodiments, the dose of active agents in the composition may be from about 200 mg to about 3 g of the compound per day, for example, from about 500 mg to about 3 g of the compound per day, or from about 750 mg to about 2.5 g of the compound per day, or from about 1000 mg to about 2000 mg of the compound per day. In certain embodiments, the active agent may be administered two or three times a day. In certain embodiments, each dose of active agents is no more than about 5 g, for example, no more than about 3 g, for example, no more than about 2.5 g. Each dose of the active agents may be combined with other conventional agents for the desired effect. Where the composition is for topical administration, the concentration of the compound may be from about 0.01 g to about 0.5 g per $cm^2$ of skin, or from about 0.1 g to about 0.4 g or from about 0.2 g to about 0.3 g per $cm^2$ of skin.

The compounds and pharmaceutical compositions described herein may, for example, be used for treating a microbial infection and/or for treating inflammation and/or for reducing the formation of blood clots and/or for treating a wound and/or for treating cystic fibrosis and/or for treating epidermolysis bullosa. For example, the compounds and pharmaceutical compositions described herein may be used for treating a wound in a subject having epidermolysis bullosa. These uses may, for example, be therapeutic or non-therapeutic.

The compounds and pharmaceutical compositions described herein may be used as an antimicrobial. As used herein, the term "antimicrobial" means that the compositions and pharmaceutical compositions described herein may be used to kill microbes, to inhibit bacterial motility, for example swarming, swimming or twitching, and/or to inhibit the growth of microbes and/or to reduce the growth of microbes.

The compounds and pharmaceutical compositions described herein may be used to inhibit and/or eradicate bacterial biofilm formation. The inhibition and/or eradication of bacterial biofilm formation may, for example, be the result of the inhibition of bacterial signalling, for example quorum sensing, inhibition of the formation or dispersal of bacterial biofilms, inhibition or stimulation of global regulatory systems (for example those dependent upon intracellular levels of cyclic dimeric guanosine monophosphate), and inhibition of the formation of functional bacterial cell surface and excreted proteins.

In certain embodiments, the microbes may be selected from bacteria, fungi, and protozoa. The bacterial strains may, for example, be selected from gram positive bacteria, gram negative bacteria, and atypical bacteria. The gram positive bacteria may, for example, be selected from one or more of *Clostridium perfringens, Listeria monocytogenes, Bacillus cereus, Enterococcus faecalis, Staphylococcus aureus*, Methicillin-resistant *Staphylococcus aureus, Staphylococcus epidermidis, Streptococcus pneumoniae, Streptococcus pyogenes, Clostridium* spp., and *Peptostreptococcus* spp.

The gram negative bacteria may, for example, be selected from one or more of *Salmonella Typhimurium Vibrio parahaemolyticus*, Enterobacteriae, for example, *Escherichia coli, Klebsiella pneumoniae, Enterobacter* spp., *Proteus* spp., *Citrobacter* spp., *Morganella morganii, Pseudomonas aeruginosa, Acinetobacter baumannii, Campylocateri jejuni, Bacteroides* spp., *Prevotella* spp., *Helicobacter pylori*, and *Porphyromonas* spp. The atypical bacteria may, for example, be selected from one or more of *Mycoplasma* pneumonia, *Chlamydia* pneumonia, *Legionella pneumophila*, and mycobacteria. The fungal strains may, for example, be selected from one or more of *Candida albicans, Candida glabrata, Aspergillus fumigatus*.

The bacterial strains may be a biofilm forming bacteria and/or a bacteria capable of forming biofilm. The biofilm forming bacteria and/or bacteria capable of forming biofilm may, for example, be selected from *Bacillus* spp, *Listeria monocytogenes, Staphylococcus aureus, Lactobacillus plantarum, Lactococcus lactis, Vibrio fischeri, Aeromonas hydrophila, Aeromonas salmonicida, Agrobacterium tumefaciens, Burkholderia cepacia, Chromobacterium violaceum, Enterobacter agglomerans, Erwinia carotovora, Erwinia chrysanthemi, Erwinia Stewartii, Escherichia coli, Helicobacter pylori, Pseudomonas aureofaciens, Pseudomonas aeruginosa, Ralstonia solanacearum, Rhizobium etli, Rhizobium leguminosarum, Rhodobacter sphaeroides, Salmonella typhimurium, Serratia liquefaciens, Sinorhizobium meliloti, Vibrio anguillarum, Vibrio harveyi, Yersinia enterocolitica, Yersinia pseudotuberculosis*.

For example, the compounds and pharmaceutical compositions described herein may be administered to a subject to treat and/or prevent a microbial infection in a subject. For example, the compounds and pharmaceutical compositions described herein may be used to facilitate healing of damaged wound on the skin. For example, the compounds and pharmaceutical compositions described herein may be used to prevent microbial infection of damaged skin. For example, the compounds and pharmaceutical compositions described herein may be used to treat or prevent a microbial infection in the digestive system. For example, the compounds and pharmaceutical compositions described herein may be used to treat or prevent a microbial infection in the nasal or aural cavity of a subject. For example, the compounds and pharmaceutical compositions described herein may be used treat or prevent a microbial infection in the respiratory tract of a subject. For example, the compounds and pharmaceutical compositions described herein may be used treat or prevent a microbial infection in the respiratory tract of a cystic fibrosis patient. For example, the compounds and pharmaceutical compositions described herein may be used as a urinary tract rinse or a bladder rinse, for example for urinary tract implant, indwelling urinary catheter, and kidney dialysis patients.

Thus, there is provided herein a therapeutic use of a compound or pharmaceutical composition described herein as an antimicrobial. There is also provided herein a compound or pharmaceutical composition as described herein for use as an antimicrobial. There is further provided herein a use of a composition or pharmaceutical composition as described herein in the manufacture of an antimicrobial medicament. There is further provided herein a therapeutic method for treating and/or preventing a microbial infection in a subject, the method comprising administering a compound or pharmaceutical composition as described herein to the subject.

In certain embodiments, the compounds and pharmaceutical compositions disclosed herein are used in non-therapeutic applications.

For example, the compounds described herein may be used as an antimicrobial agent on non-living surfaces (e.g. as a disinfectant). For example, the compounds and pharmaceutical compositions disclosed herein may be used for cosmetic applications, for example as an antimicrobial agent on living surfaces (e.g. skin). For example, the compounds and pharmaceutical compositions disclosed herein may be used as an antimicrobial in cosmetic skincare compositions or makeup compositions.

For example, the compounds described herein may be used as an antimicrobial agent on industrial non-living surface, for example to remove or prevent biofilm formation in piping used in the water or oil industries, as a cleaning agent for water tanks (e.g. in fisheries), as an anti-fowling agent in industrial processes (e.g. water industries, fisheries).

For example, the compounds described herein may be used as food and/or water additives for preservation and/or prevention of disease transmission. For example, the compounds described herein may be used in plant, fresh fruit and vegetable washes. The compounds described herein may reduce surface bacteria, extend shelf life and/or protect the surface from pest invasion in live crops or agricultural produce.

For example, the compounds described herein may be used as an antimicrobial in medical devices or medical compositions, for example in cements for bone or dental implants, in implants, in wound dressings, in stitches, or in threads.

For example, the compounds described herein may be used as an antimicrobial on living surface. For example, the compounds described herein may be applied to the skin to kill microbes or inhibit growth of microbes for hygiene reasons (e.g. to prevent spread of disease). For example, the compounds described herein may be applied to the hands as a hand sanitizer. For example, the compounds described herein may be used as an oral rinse, for example to treat or prevent halitosis. For example, the compounds described herein may be used as a dental care product, for example to treat or prevent cavities and plague.

For example, the compounds described herein may be used for agricultural applications. For example, the compounds described herein may be used to treat or prevent infection of plant micro-wounds or may be used to reduce surface pathogens on a plant. For example, the compounds described herein may be used as bio-security sanitizer, for example for animal farm facilities. For example, the compounds described herein may be used for animal feed sterilization.

The compounds and pharmaceutical compositions described herein may be used as an anti-inflammatory agent. A used herein, the term "anti-inflammatory" means that the compositions and pharmaceutical compositions described herein may be used to reduce inflammation or swelling.

For example, the compounds and pharmaceutical compositions described herein may be administered to a subject to treat and/or prevent inflammation in a subject. Thus, there is provided herein a therapeutic use of a compound or pharmaceutical composition described herein as an anti-inflammatory. There is also provided herein a compound or pharmaceutical composition as described herein for use as an anti-inflammatory. There is further provided herein a use of a composition or pharmaceutical composition as described herein in the manufacture of an anti-inflammatory medicament. There is further provided herein a therapeutic method for treating and/or preventing inflammation in a subject, the method comprising administering a compound or pharmaceutical composition as described herein to the subject.

The compounds and pharmaceutical compositions described herein may therefore be used to treat or prevent an inflammatory disease or disorder. Examples of inflammatory diseases or disorders include, for example, allergies, cancer, atherosclerosis, ischemic heart disease, acne vulgaris, asthma, autoimmune diseases, autoinflammatory diseases, celiac disease, chronic prostatitis, colitis, diverticulitis, glomerulonephritis, hidradenitis suppurativa, hypersensitivities, inflammatory bowel diseases, interstitial cystitis, lichen planus, mast cell activation syndrome, mastocytosis, otitis, pelvic inflammatory disease, reperfusion injury, rheumatic fever, rheumatoid arthritis, rhinitis, sarcoidosis, transplant rejection, and vasculitis.

Treatment of inflammation may, for example, be determined by measuring the expression level of one or more inflammation markers such as, for example, C-reactive protein (CRP) and erythrocyte sedimentation rate (ESR). A reduction in CRP and ESR expression indicates a reduction of inflammation.

The compounds and pharmaceutical compositions described herein may be used as an anti-thrombotic agent. A used herein, the term "anti-thrombotic" means that the compositions and pharmaceutical compositions described herein may be used to reduce the formation of blood dots, for example by inhibiting platelet aggregation. The anti-thrombotic may therefore be used to increase blood flow in a subject.

For example, the compounds and pharmaceutical compositions described herein may be administered to a subject to reduce the formation of blood clots in a subject. Thus, there is provided herein a therapeutic use of a compound or pharmaceutical composition described herein as an anti-thrombotic. There is also provided herein a compound or pharmaceutical composition as described herein for use as an anti-thrombotic. There is further provided herein a use of a composition or pharmaceutical composition as described herein in the manufacture of an anti-thrombotic medicament. There is further provided herein a therapeutic method for reducing the formation of blood clots in a subject, the method comprising administering a compound or pharmaceutical composition as described herein to the subject.

The compounds and pharmaceutical compositions described herein may therefore be used to treat or prevent a disorder associated with blood flow in a subject. The compounds and pharmaceutical compositions disclosed herein may be used to improve (e.g. increase) blood flow in a subject, for example in a subject that has a blood flow level that is outside what is considered to be a normal or healthy range. For example, the compounds and pharmaceutical compositions disclosed herein may be used to treat or prevent any disease or disorder associated with blood flow (e.g. circulation system) in a subject. For example, the subject may be susceptible to developing one or more diseases or disorders associated with blood flow.

Diseases and disorders associated with blood flow and/or platelet aggregation include, for example, cardiovascular diseases, cerebrovascular or brain disease, immune diseases, bone, joint and/or muscle diseases and fatigue diseases.

Cardiovascular diseases and disorders include, for example, coronary artery diseases, coronary heart disease, angina, myocardial infarction, hypertensive heart disease, heart failure, pulmonary heart disease, cardiac dysrhythmias, inflammatory heart disease, rheumatic heart disease, cardiomyopathy, atrial myopathy, congenital heart disease, endocarditis, inflammatory cardiomegaly, myocarditis, valvular heart disease, aortic aneurysms, venous thrombosis, rheumatoid vasculitis, atherosclerosis peripheral artery diseases and renal artery stenosis.

Cerebrovascular diseases and brain diseases include, for example, stroke (e.g. mini-stroke, hemorrhagic stroke, ischemic stroke), transient ischemic attack (TIA), subarachnoid haemorrhage and vascular dementia.

Immune diseases and disorders include, for example, any disease in which the subject's immune response is lower than a normal healthy individual, for example immunodeficiency diseases (e.g. primary, secondary, humoral, T cell, neutropenia, asplenia and complement deficiency diseases), low immune response in subjects whose immune system has been compromised (e.g. subjects undergoing chemotherapy and/or radiotherapy, subjects infected with HIV, subjects missing one or more organs associated with immune function such as the spleen, tonsils, lymph nodes). For example, immune diseases include ataxia-telangiectasia, Chediak-Higashi syndrome, combined immunodeficiency disease, complement deficiencies, DiGeorge syndrome, hypogammaglobulinemia, Job syndrome, leukocyte adhesion defects, panhypogammaglobulinemia, Bruton's disease, congenital agammaglobulinemia, selective deficiency of IgA, Wiskott-Aldrich syndrome and severe combined immunodeficiency disorder (SCID). For example, infection or symptoms related to immune health include upper and lower respiratory tract infection, hay fever, sinus and pharyngitis.

Joint diseases and disorders include, for example, any disease related to joints, mobility, muscle and bone health, for example arthritis (e.g. osteoarthritis, rheumatoid arthritis, psoriatic arthritis, septic arthritis), bursitis, osteonecrosis, dislocations, Perthes disease and Paget's disease of the bone.

Fatigue diseases and disorders include, for example, simple fatigue and/or any disease in which fatigue is a symptom. For example, fatigue diseases and disorders include chronic fatigue syndrome, anaemia, depression, iron deficiency (without anaemia), sleep disorders, underactive thyroid, overactive thyroid, Addison disease, anorexia nervosa or other eating disorders, autoimmune diseases such as lupus, diabetes, fibromyalgia, kidney disease, liver disease and malnutrition.

In certain embodiments, the compound or pharmaceutical composition described herein may be used for maintaining and/or improving the overall health of the circulatory system, for example to treat or reduce or prevent the onset of one or more circulatory system-associated diseases or disorders, and/or to provide beneficial effects to the metabolic system via the maintenance or improvement of healthy blood flow.

The compounds and pharmaceutical compositions described herein may be used in various non-therapeutic applications.

For example, the compounds and pharmaceutical compositions may be used in methods of maintaining blood flow in a subject. For example, where a subject is healthy or has a normal blood flow level, and may, for example, not be at any particular risk of developing any disease associated with blood flow, the subject may consume the compositions disclosed herein to maintain a normal blood flow level. For example, where a subject is healthy and may, for example, not be at any particular risk of developing any disease associated with blood flow and/or platelet aggregation, the subject may consume the compositions disclosed herein as part of a healthy lifestyle.

The anti-thrombotic activity of a compound may, for example, be measured by determining the degree of platelet aggregation, for example using an optical aggregometer.

The compounds and pharmaceutical compositions described herein may be used as an agent to promote wound healing (e.g. to cause or accelerate healing of a wound).

For example, the compounds and pharmaceutical compositions described herein may be administered to a subject as a wound treatment agent. Thus, there is provided herein a therapeutic use of a compound or pharmaceutical composition described herein to treat a wound. There is also provided herein a compound or pharmaceutical composition as described herein for use as wound treatment agent. There is further provided herein a use of a composition or pharmaceutical composition as described herein in the manufacture of a wound treatment agent. There is further provided herein a therapeutic method for healing a wound in a subject, the method comprising administering a compound or pharmaceutical composition as described herein to the subject.

The compounds and pharmaceutical compositions described herein may therefore be used to treat or prevent a disorder associated with a wound in a subject. The compounds and pharmaceutical compositions disclosed herein may be used to improve (e.g. increase) wound healing in a subject, for example in a subject that has increased number and/or severity of wounds compared to a healthy individual or has delayed, incomplete, or non-typical healing of wounds compared to a healthy individual. For example, the compounds and pharmaceutical compositions disclosed herein may be used to treat or prevent any disease or disorder associated wound healing in a subject. For example, the compounds and pharmaceutical compositions disclosed herein may be used to treat or prevent a wound in a subject having a disease or disorder that results in delayed, incomplete or non-typical wound healing in the subject. For example, the subject may be susceptible to developing one or more diseases or disorders associated with wound healing.

Diseases and disorders associated with wound healing or resulting in delayed, incomplete or non-typical wound healing in a subject include, for example, epidermolysis bullosa, diabetes (type 1 or type 2), anaemia, circulatory disorders, Ehlers-Danlos Syndrome (EDS), eczema and skin ulcers.

The compounds and pharmaceutical compositions described herein may be used as an anti-cancer agent. Thus, the compounds and pharmaceutical compositions described herein may therefore be used to treat or prevent cancer.

Methods for Making a Compound of Formula (I)

The compounds of formula (I) and the pharmaceutical compositions comprising a compound of formula (I) may be made by any suitable method.

In certain embodiments, the pharmaceutical compositions are made by combining a compound of formula (I) with a pharmaceutically acceptable carrier and/or excipient and/or diluent. The components are combined in suitable amounts to obtain a composition having the desired quantity and concentration of each component. Each component may be combined with one or more other components in any order and combination suitable to obtain the desired product. For example, each component may be combined by mixing. Such methods are well known in the art, for example, methods known in the pharmaceutical industry. The pharmaceutical composition may be prepared in the dry solid form, for example, powder form, and subject to further processing steps depending on the types of the formulation for the intended finished products. The methods may further comprise a forming step, wherein the mixture is moulded, pressed, spray dried or otherwise formed into a shape (e.g. bar, ball, pellet, clusters, tablet), preferably with dimensions and/or textures suitable for consumption by a human or other mammalian animal of the types described herein.

In certain embodiments, the method for making the compounds of formula (I) may proceed via the following reaction scheme.

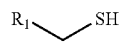

with propargyl bromide.

The reaction of step 1 may take place in the presence of a hydroxide and alcohol. The hydroxide may, for example, be potassium hydroxide. The alcohol may, for example, be an organic alcohol such as methanol.

Step 1 may, for example, comprise bubbling nitrogen through the reaction mixture. The reaction mixture of step 1 may, for example, have a temperature equal to or less than about 20° C., for example equal to or less than about 10° C., for example about 5° C.

The reaction of step 1 may, for example, form a precipitated product. The reaction mixture may, for example, be warmed to room temperature before the product is purified.

Purification of the product of step 1 may, for example, comprise removing the solvent in vacuo. The residue may then be partitioned between water and an organic compound such as tert-butyl methyl ether. The aqueous layer may, for example, be extracted for a second time using more organic compound such as tert-butyl methyl ether. The organic layers may then be washed with water and brine (e.g. sodium chloride), dried (e.g. over sodium sulphate), filtered and then concentrated (e.g. under reduced pressure).

In certain embodiments, step 2 comprises reacting

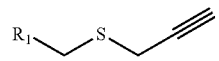

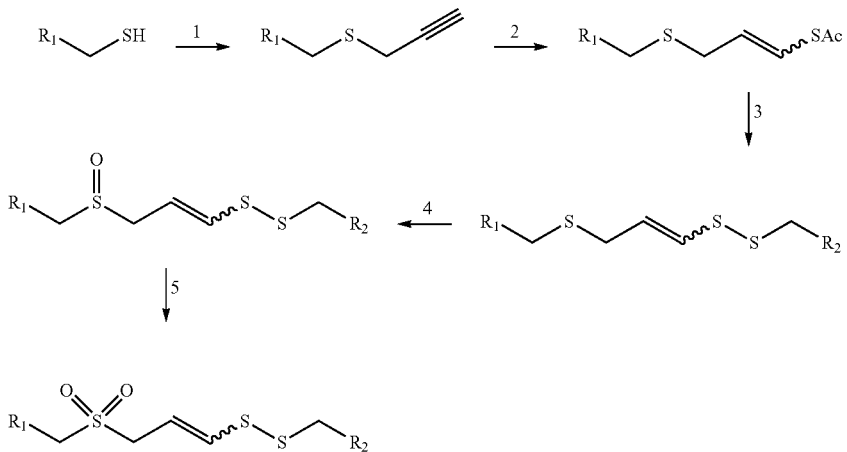

In certain embodiments, step 1 comprises reacting

with a compound comprising propargyl. For example, step 1 comprises reacting

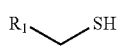

with a propargyl halide. For example, step 1 comprises reacting with thioacetic acid. The thioacetic acid may, for example, be present in an organic solvent such as toluene.

The product of step 1 may, for example, be present in an organic solvent such as toluene. This may, for example, be degassed with nitrogen. 2,2'-Azobis(2-methylpropionitrile) or 1,1'-Azobis(cyanocyclohexane) (ACHN) may be used as a radical initiator in step 2.

The reaction mixture of step 2 may, for example, have a temperature equal to or greater than about 50° C. or equal to or greater than about 60° C. For example, the reaction mixture of step 2 may have a temperature ranging from about 50° C. to about 100° C., for example from about 60° C. to about 90° C., for example from about 70° C. to about 80° C.

After the product of step 2 has been made, the reaction mixture may be cooled to room temperature before the product is purified.

Purification of the product of step 2 may, for example, comprise removing the solvent in vacuo. The crude residue may, for example, be purified (e.g. purified twice) via silica gel flash column chromatography, for example using heptane:ethyl acetate 10% as a solvent system.

In certain embodiments, step 3 comprises reacting

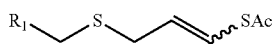

with $R_2$-tosylate or $R_2$-mesylate. The $R_2$-tosylate may, for example, be present in an organic solvent such as methanol and/or tetrahydrofuran.

The product of step 2 may, for example, be present in an organic solvent such as methanol. The reaction of step 1 may take place in the presence of a hydroxide and alcohol. The hydroxide may, for example, be potassium hydroxide. The alcohol may, for example, be an organic alcohol such as methanol.

The temperature of the reaction mixture of step 3 may, for example, be equal to or less than about 0° C., for example equal to or less than about −10° C. or equal to or less than about −20° C. or equal to or less than about −30° C. or equal to or less than about −40° C., for example ranging from about −80° C. to about −20° C. or from about −60° C. to about −30° C. or from about −50° C. to about −30° C.

After the product of step 3 has been made, the reaction mixture may be warmed to room temperature before the product is purified.

Purification of the product of step 2 may, for example, comprise adding an aqueous solution of ammonium chloride to the reaction mixture. The product of step 3 may then be extracted using an organic solvent such as ethyl acetate. The organic layers may then be washed with water and brine (e.g. sodium chloride), dried (e.g. over sodium sulphate), filtered and then concentrated (e.g. under reduced pressure). The product may then be purified via silica gel flash column chromatography, for example using heptane:ethyl acetate 2-3% as a solvent system.

In certain embodiments, step 4 comprises reacting

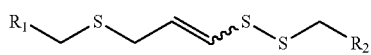

with 3-chloroperbenzoic acid or other oxidising agents.

The product of step 3 may, for example, be present in an organic solvent such as dichloromethane.

The temperature of the reaction mixture of step 4 may, for example, be equal to or less than about −20° C., for example equal or less than about −30° C., for example equal to or less than about −40° C., for example equal to or less than about −50° C. For example, the temperature of the reaction mixture of step 4 may be from about −80° C. to about −20° C. or from about −70° C. to about −40° C. or from about −70° C. to about −50° C.

The reaction mixture may, for example, be warmed to room temperature before the product is purified.

Purification of the product of step 4 may, for example, comprise partitioning the reaction mixture between a half saturated aqueous solution of a weak base such as sodium bicarbonate and dichloromethane. The aqueous layer may further be extracted using an organic solvent, for example dichloromethane. The organic layers may then be dried (e.g. over magnesium sulphate), filtered and concentrated (e.g. in vacuo). The product may then be purified via silica gel flash column chromatography, for example using dichloromethane:ethyl acetate 0-5% as the solvent system.

In certain embodiments, step 5 comprises reacting

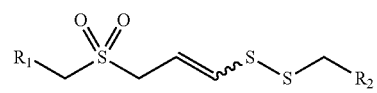

with a permanganate such as potassium permanganate or another oxidising agent. The permanganate may, for example, be in an organic solvent such as acetone.

The reaction mixture may, for example, comprise an organic solvent such as acetone. The reaction mixture may, for example, comprise a drying agent such as magnesium sulphate.

The temperature of the reaction mixture of step 5 may, for example, be equal to or less than about 0° C., for example equal to or less than about −10° C. or equal to or less than about −20° C. or equal to or less than about −30° C. or equal to or less than about −40° C., for example ranging from about −80° C. to about −20° C. or from about −60° C. to about −30° C. or from about −50° C. to about −30° C.

The reaction mixture may, for example, be filtered (e.g. through a pad of celite) and washed with an organic solvent (e.g. acetone). The filtrates may be concentrated under reduced pressure. The product may be purified, for example via silica gel flash column chromatography, for example using hexane:ethyl acetate 10-30% as the solvent system.

EXAMPLES

Example 1—Method of Preparation of 1-Allyl-2-(3-((4-(trifluoromethyl)benzyl)sulfonyl)prop-1-en-1-yl) disulfane

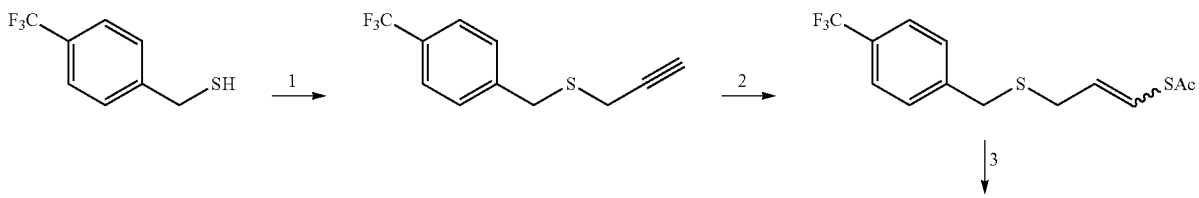

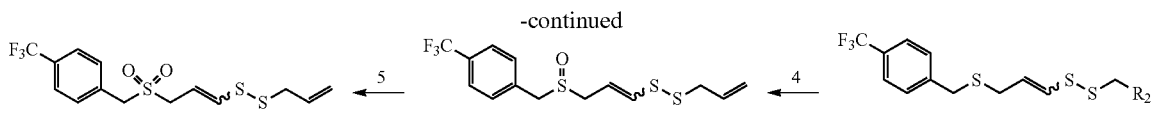

Step 1—Preparation of Prop-2-yn-1-yl(4-(trifluoromethyl)benzyl)sulfane

A solution of potassium hydroxide (7.02 g, 125.00 mmol) in methanol (240 mL) was stirred whilst bubbling nitrogen through for 20 min, in a 3-neck round-bottom flask, the solution was cooled to 5° C. in an ice/salt bath. Then, (4-(trifluoromethyl)phenyl)methane thiol (20.02 g, 104.30 mmol) was added dropwise using a pressure-equalising dropping funnel over a period of 15 min. and the resulting reaction mixture was stirred for a further 20 min. After that time, propargyl bromide (17.4 mL, 156.00 mmol) was added dropwise to the mixture via a syringe, over a period of 20 min, a precipitate was observed. The reaction mixture was warmed to room temperature and was stirred for another 2 h.

Solvent was removed under reduced pressure, and the residue was partitioned between water (300 mL) and tert-butyl methyl ether (200 mL). The aqueous layer was extracted again with more tert-butyl methyl ether (2×200 mL). The organic layers were combined, washed with water (2×200 mL) and brine (200 mL), dried over sodium sulfate, filtered and concentrated under reduced pressure in order to afford the desired product, prop-2-yn-1-yl(4-(trifluoromethyl)benzyl)sulfane, as a pale yellow oil (23.09 g, 96% yield).

Step 2—Preparation of S-(3-((4-(Trifluoromethyl)benzyl)thio)prop-1-en-1-yl) ethanethioate A solution of prop-2-yn-1-yl(4-(trifluoromethyl)benzyl)sulfane (23.09 g, 100.40 mmol) in toluene (400 mL) was degassed with nitrogen for 20 min. 2,2'-Azobis(2-methylpropionitrile) (824 mg, 5.02 mmol) was added to the previous solution and degassing was continued whilst the reaction mixture was heated to 75° C. (internal temperature). A solution of thioacetic acid (7.6 mL, 105.70 mmol) in toluene (100 mL), was then added dropwise to the reaction mixture over a period of 2 h. The mixture was stirred for 18 h under these conditions.

The reaction mixture was cooled to room temperature and solvent was removed in vacuo. The crude residue was purified twice via silica gel flash column chromatography using heptane:ethyl acetate 10% as solvent system in order to afford the desired product, S-(3-((4-(trifluoromethyl)benzyl)thio)prop-1-en-1-yl) ethanethioate (6.4 g).

Step 3—Preparation of 1-Allyl-2-(3-((4-(trifluoromethyl)benzyl)thio)prop-1-en-1-yl)disulfane A solution of S-(3-((4-(trifluoromethyl)benzyl)thio)prop-1-en-1-yl) ethanethioate (3.16 g, 10.33 mmol) in methanol (60 mL) was cooled to −30° C. in an acetonitrile/cardice bath, under nitrogen. A 1M solution of potassium hydroxide in methanol (12.4 mL, 12.40 mmol) was added to the previous solution dropwise over a period of 15 min. The reaction mixture was stirred for 30 min. Then the mixture was cooled further to −65° C. and it was stirred for 15 min. followed by the addition of a solution of S-allyl tosylate (2.83 g, 12.4 mmol) in methanol (40 mL), added dropwise over a period of 30 min. The mixture was stirred for a further 1.5 h. LCMS Analysis showed the reaction had gone to completion.

A saturated aqueous solution of ammonium chloride (10 mL) was added dropwise to the reaction mixture, and it was warmed to room temperature. The mixture was poured into a saturated aqueous solution of ammonium chloride (400 mL) and it was extracted with ethyl acetate (3×200 mL). The organic layers were combined together and washed with water and brine, dried over sodium sulfate, filtered and concentrated under reduced pressure. The crude residue was purified via silica gel flash column chromatography using heptane:ethyl acetate 2-5% as solvent system in order to afford the desired product 1-allyl-2-(3-((4-(trifluoromethyl)benzyl)thio)prop-1-en-1-yl) disulfane (3.1 g).

Step 4—Preparation of 1-Allyl-2-(3-((4-(trifluoromethyl)benzyl)sulfinyl)prop-1-en-1-yl)disulfane 3-Chloroperbenzoic acid (77%) (2.17 g, 9.67 mmol) was added in four portions to a stirring solution of 1-allyl-2-(3-((4-(trifluoromethyl)benzyl)thio)prop-1-en-1-yl)disulfane (3.10 g, 9.21 mmol) in dichloromethane (75 mL) at −78° C. The reaction mixture was slowly warmed to −20° C. over a period of 1.5 h, it was stirred at this temperature for 1 h and at room temperature for another hour. LCMS Analysis showed the reaction had reached completion.

The reaction mixture was quenched with a saturated aqueous solution of sodium bicarbonate (50 mL) and it was extracted with dichloromethane (3×100 mL). The organic layers were combined together, dried over sodium sulfate, filtered and concentrated under reduced pressure. The crude material was purified via silica gel flash column chromatography using heptane:dichloromethane 50% and heptane:ethyl acetate 5% as solvent systems in order to afford the desired product, 1-allyl-2-(3-((4-(trifluoromethyl)benzyl)sulfinyl)prop-1-en-1-yl)disulfane (2.67 g).

Step 5—Preparation of 1-Allyl-2-(3-((4-(trifluoromethyl)benzyl)sulfonyl)prop-1-en-1-yl)disulfane 1-Allyl-2-(3-((4-(trifluoromethyl)benzyl)sulfinyl)prop-1-en-1-yl)disulfane (2.65 g, 7.52 mmol) was dissolved in acetone (75 mL) at room temperature in a three neck round-bottom flask fitted with a thermometer and nitrogen inlet. Magnesium sulfate (9.96 g, 8.27 mmol) was added to the previous solution and it was cooled to −40° C. A solution of potassium permanganate (2.67 g, 16.92 mmol) in acetone (100 mL) was added dropwise over a period of 50 min. keeping the temperature below −30° C. More acetone (25 mL) was used in order to wash in undissolved potassium permanganate. The reaction mixture was stirred at −25° C. overnight.

LCMS Analysis showed the reaction had gone to completion. The reaction mixture was warmed to room temperature and it was filtered through a pad of celite, which was washed several times with acetone. The filtrates were concentrated under reduced pressure in order to afford 1.9 g of crude material. Due to a slightly low recovery the celite pad was washed with further portions of acetone and with dichloromethane, but this did not yield any significant amount of product. The previously isolated crude material was purified via silica gel flash column chromatography using hexane:ethyl acetate 20% as solvent system in order to afford the desired product, 1-allyl-2-(3-((4-(trifluoromethyl)benzyl) sulfonyl)prop-1-en-1-yl)disulfane, as a white solid with a (66:34) (Z:E) ratio (1.50 g).

Example 2—Method of Preparation of 1-(4-Methoxybenzyl)-2-(3-((4-(trifluoromethyl)benzyl) sulfonyl)prop-1-en-1-yl)disulfane A solution of thioacetic acid (7.6 mL, 105.70 mmol) in toluene (100 mL), was then added dropwise to the reaction mixture over a period of 2 h. The mixture was stirred for 18 h under these conditions.

The reaction mixture was cooled to room temperature and solvent was removed in vacuo. The crude residue was purified twice via silica gel flash column chromatography using heptane:ethyl acetate 10% as solvent system in order to afford the desired product, S-(3-((4-(trifluoromethyl)benzyl)thio)prop-1-en-1-yl) ethanethioate (6.4 g).

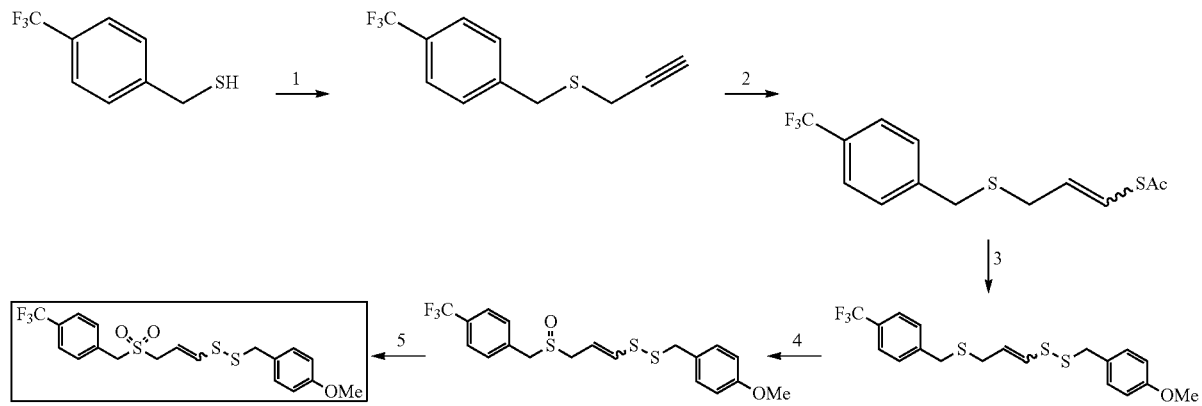

Step 1—Preparation of Prop-2-yn-1-yl(4-(trifluoromethyl)benzyl)sulfane

A solution of potassium hydroxide (7.02 g, 125.00 mmol) in methanol (240 mL) was stirred whilst bubbling nitrogen through for 20 min, in a 3-neck round-bottom flask, the solution was cooled to 5° C. in an ice/salt bath. Then, (4-(trifluoromethyl)phenyl)methane thiol (20.02 g, 104.30 mmol) was added dropwise using a pressure-equalising dropping funnel over a period of 15 min. and the resulting reaction mixture was stirred fora further 20 min. After that time, propargyl bromide (17.4 mL, 156.00 mmol) was added dropwise to the mixture via a syringe, over a period of 20 min, a precipitate was observed. The reaction mixture was warmed to room temperature and was stirred for another 2 h.

Solvent was removed under reduced pressure, and the residue was partitioned between water (300 mL) and tert-butyl methyl ether (200 mL). The aqueous layer was extracted again with more tert-butyl methyl ether (2×200 mL). The organic layers were combined, washed with water (2×200 mL) and brine (200 mL), dried over sodium sulfate, filtered and concentrated under reduced pressure in order to afford the desired product, prop-2-yn-1-yl(4-(trifluoromethyl)benzyl)sulfane, as a pale yellow oil (23.09 g, 96% yield).

Step 2—Preparation of S-(3-((4-(Trifluoromethyl) benzyl)thio)prop-1-en-1-yl) ethanethioate A solution of prop-2-yn-1-yl(4-(trifluoromethyl)benzyl) sulfane (23.09 g, 100.40 mmol) in toluene (400 mL) was degassed with nitrogen for 20 min. 2,2'-Azobis(2-methyl-propionitrile) (824 mg, 5.02 mmol) was added to the previous solution and degassing was continued whilst the reaction mixture was heated to 75° C. (internal temperature).

Step 3—Preparation of 1-(4-Methoxybenzyl)-2-(3-((4-(trifluoromethyl)benzyl)thio)prop-1-en-1-yl) disulfane A solution of S-(3-((4-(trifluoromethyl)benzyl)thio)prop-1-en-1-yl) ethanethioate (3.06 g, 10.00 mmol) in methanol (100 mL) was cooled to −44° C. in an acetonitrile/cardice bath, under nitrogen. A 1M solution of potassium hydroxide in methanol (12 mL, 12.00 mmol) was added to the previous solution dropwise keeping the internal temperature at −37° C. The reaction mixture was stirred for 30 min. Then the mixture was cooled further to −70° C. in an acetone/cardice bath. A solution of S-(4-methoxybenzyl) 4-methylbenzene-sulfonothioate (4.63 g, 15.00 mmol) in tetrahydrofuran (100 mL) was added dropwise using a dropping funnel, keeping the temperature below −65° C. The mixture was stirred for a further 2 h at that temperature and at room temperature for another 2 h.

The reaction mixture was partitioned between tert-butyl-methyl ether (500 mL) and a half saturated aqueous solution of ammonium chloride (500 mL). The aqueous layer was further extracted with tert-butylmethyl ether (2×200 mL). The organic layers were combined together, dried over sodium sulfate, filtered and concentrated under reduced pressure. The crude residue was purified via silica gel flash column chromatography using hexane:ethyl acetate 2% as solvent system in order to afford the desired product, 1-(4-methoxybenzyl)-2-(3-((4-(trifluoromethyl)benzyl)thio) prop-1-en-1-yl)disulfane (4.02 g).

Step 4—Preparation of 1-(4-Methoxybenzyl)-2-(3-((4-(trifluoromethyl)benzyl)sulfinyl)prop-1-en-1-yl) disulfane 3-Chloroperbenzoic acid (77%) (2.67 g, 11.50 mmol) was added in portions to a stirring solution of 1-(4-methoxybenzyl)-2-(3-((4-(trifluoromethyl)benzyl)thio)prop-1-en-1-yl) disulfane (4.02 g, 9.60 mmol) in dichloromethane (60 mL) at −70° C. The temperature increased by 5° C. The reaction mixture was slowly warmed to room temperature overnight.

The reaction mixture was partitioned between dichloromethane (50 mL) and a half saturated aqueous solution of sodium bicarbonate (100 mL). The aqueous layer was further extracted with dichloromethane (2×50 mL). The organic layers were combined together, dried over sodium sulfate, filtered and concentrated under reduced pressure. The crude material was purified via silica gel flash column chromatography using dichloromethane:ethyl acetate 3-5% as solvent system in order to afford the desired product 1-(4-methoxybenzyl)-2-(3-((4-(trifluoromethyl)benzyl)sulfinyl) prop-1-en-1-yl)disulfane (4.05 g).

Step 5—Preparation of 1-(4-Methoxybenzyl)-2-(3-((4-(trifluoromethyl)benzyl)sulfonyl)prop-1-en-1-yl) disulfane 1-(4-Methoxybenzyl)-2-(3-((4-(trifluoromethyl)benzyl) sulfinyl)prop-1-en-1-yl)disulfane (4.05 g, 9.36 mmol) was dissolved in acetone (35 mL) at room temperature in a three neck round-bottom flask fitted with a thermometer and nitrogen inlet. Magnesium sulfate (12.61 g, 105.00 mmol) was added to the previous solution and it was cooled to −35° C. A solution of potassium permanganate (3.35 g, 21.20 mmol) in acetone (350 mL) was added dropwise with a dropping funnel over a period of 40 min., keeping the internal temperature below −25° C. The reaction mixture was stirred at −24° C. overnight.

The reaction mixture was warmed to room temperature and it was filtered through a pad of celite, which was washed several times with acetone (500 mL). The filtrates were concentrated under reduced pressure. The crude material was purified via silica gel flash column chromatography (with a 120 g cartridge), using toluene (40 mL) and a little bit of dichloromethane to load the material onto the column and hexane:ethyl acetate 10-20% as solvent system in order to afford the desired product, 1-(4-methoxybenzyl)-2-(3-((4-(trifluoromethyl)benzyl) sulfonyl)prop-1-en-1-yl)disulfane, as a colourless solid with a (3:1) (Z:E) ratio (1.70 g).

Example 3—Method of preparation of 1-(3-Methoxybenzyl)-2-(3-((4-(trifluoromethyl)benzyl) sulfonyl)prop-1-en-1-yl)disulfane Step 1—Preparation of Prop-2-yn-1-yl(4-(trifluoromethyl)benzyl)sulfane A solution of potassium hydroxide (7.02 g, 125.00 mmol) in methanol (240 mL) was stirred whilst bubbling nitrogen through for 20 min, in a 3-neck round-bottom flask, the solution was cooled to 5° C. in an ice/salt bath. Then, (4-(trifluoromethyl)phenyl)methane thiol (20.02 g, 104.30 mmol) was added dropwise using a pressure-equalising dropping funnel over a period of 15 min. and the resulting reaction mixture was stirred for a further 20 min. After that time, propargyl bromide (17.4 mL, 156.00 mmol) was added dropwise to the mixture via a syringe, over a period of 20 min, and a precipitate was observed. The reaction mixture was warmed to room temperature and was stirred for another 2 h.

Solvent was removed in vacuo, and the residue was partitioned between water (300 mL) and tert-butyl methyl ether (200 mL). The aqueous layer was extracted again with more tert-butyl methyl ether (2×200 mL). The organic layers were combined, washed with water (2×200 mL) and brine (200 mL), dried over sodium sulfate, filtered and concentrated under reduced pressure in order to afford the desired product, prop-2-yn-1-yl(4-(trifluoromethyl)benzyl)sulfane, as a pale yellow oil (23.09 g, 96% yield).

Step 2—Preparation of S-(3-((4-(Trifluoromethyl) benzyl)thio)prop-1-en-1-yl) ethanethioate A solution of prop-2-yn-1-yl(4-(trifluoromethyl)benzyl) sulfane (23.09 g, 100.40 mmol) in toluene (400 mL) was degassed with nitrogen for 20 min. 2,2'-Azobis(2-methylpropionitrile) (824 mg, 5.02 mmol) was added to the previous solution and degassing was continued whilst the reaction mixture was heated to 75° C. (internal temperature). A solution of thioacetic acid (7.6 mL, 105.70 mmol) in toluene (100 mL), was then added dropwise to the reaction mixture over a period of 2 h. The mixture was stirred for 18 h under these conditions.

The reaction mixture was cooled to room temperature and solvent was removed in vacuo. The crude residue was purified twice via silica gel flash column chromatography using heptane:ethyl acetate 10% as solvent system in order to afford the desired product, S-(3-((4-(trifluoromethyl)benzyl)thio)prop-1-en-1-yl) ethanethioate (6.4 g, 21% yield).

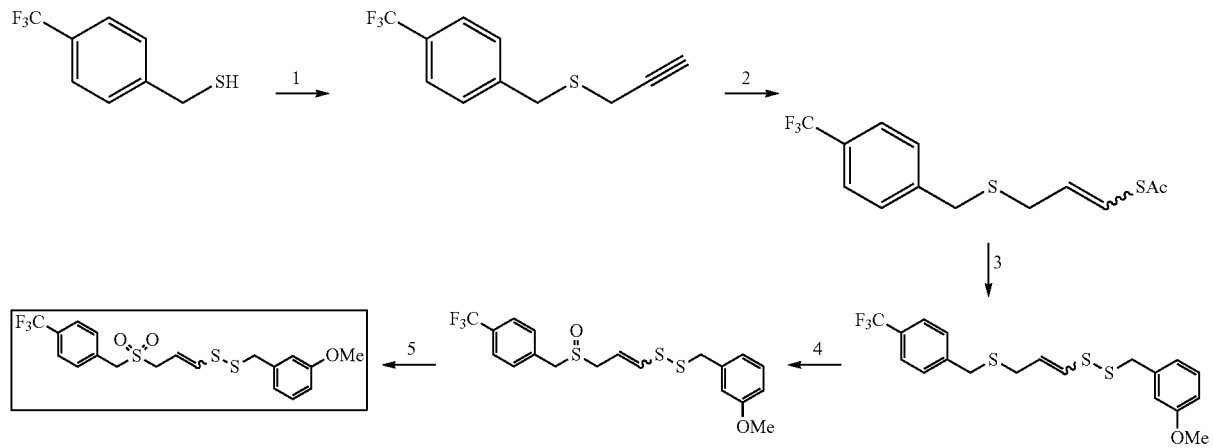

Step 3—Preparation of 1-(3-Methoxybenzyl)-2-(3-((4-(trifluoromethyl)benzyl)thio)prop-1-en-1-yl) disulfane A solution of S-(3-((4-(trifluoromethyl)benzyl)thio)prop-1-en-1-yl) ethanethioate (1.32 g, 4.31 mmol) in methanol (40 mL) was cooled to −40° C. (internal temperature) with an acetonitrile/cardice bath. A 1M solution of potassium hydroxide in methanol (5.2 mL, 5.17 mmol) was added dropwise over a period of 10 min. keeping the temperature at −40° C. The resulting mixture was stirred at this temperature for a further 30 min. then cooled to −70° C. using an acetone/cardice bath. A solution of m-methoxybenzylmercapto tosylate (1.59 g, 5.17 mmol) in methanol (20 mL) and tetrahydrofuran (4 mL) was added to the previous mixture, keeping the temperature at −65° C. The mixture was stirred for 30 min. at this temperature, then warmed to room temperature and stirred for 1 h.

A saturated aqueous solution of ammonium chloride (20 mL) was carefully added to the reaction mixture until cloudiness persisted. The mixture was then poured into a saturated aqueous solution of ammonium chloride (230 mL) and was extracted with ethyl acetate (3×100 mL). The organic extracts were combined, washed with water (100 mL) and brine (100 mL), dried over sodium sulfate, filtered and concentrated under reduced pressure in order to afford a pale yellow oil. The crude oil was purified via silica gel flash column chromatography using heptane:ethyl acetate 2-3% as solvent system in order to afford the desired product, 1-(3-methoxybenzyl)-2-(3-((4-(trifluoromethyl)benzyl)thio)prop-1-en-1-yl)disulfane, as a colourless oil (1.57 g, 87% yield).

Step 4—Preparation of 1-(3-Methoxybenzyl)-2-(3-((4-(trifluoromethyl)benzyl)sulfinyl)prop-1-en-1-yl) disulfane A solution of 1-(3-methoxybenzyl)-2-(3-((4-(trifluoromethyl)benzyl)thio)prop-1-en-1-yl)disulfane (1.57 g, 3.77 mmol) in dichloromethane (50 mL) was cooled to −65° C. 3-Chloroperbenzoic acid (1.01 g, 4.52 mmol) was added and the resulting reaction mixture was stirred for 15 min. at −65° C. and at room temperature for 3 h.

The reaction mixture was partitioned between a half saturated aqueous solution of sodium bicarbonate (50 mL) and dichloromethane. The aqueous layer was further extracted with more dichloromethane (2×25 mL). The organic layers were combined, dried over magnesium sulfate, filtered and concentrated in vacuo. The crude material was purified via silica gel flash column chromatography with a 80 g silica cartridge using dichloromethane:ethyl acetate 0-5% as solvent system in order to afford the desired product 1-(3-methoxybenzyl)-2-(3-((4-(trifluoromethyl)benzyl)sulfinyl)prop-1-en-1-yl)disulfane as an off-white solid with Z:E 71:29 (1.43 g, 88% yield).

Step 5—Preparation of 1-(3-Methoxybenzyl)-2-(3-((4-(trifluoromethyl)benzyl)sulfonyl)prop-1-en-1-yl) disulfane A solution of potassium permanganate (1.17 g, 7.40 mmol) in acetone (100 mL) was added dropwise via a dropping funnel to a mixture of 1-(3-methoxybenzyl)-2-(3-((4-(trifluoromethyl)benzyl)sulfinyl)prop-1-en-1-yl) disulfane (1.41 g, 3.26 mmol) and magnesium sulfate (4.40 g, 36.60 mmol) in acetone (100 mL), previously cooled to −45° C., over a period of 15 min. keeping the temperature below −25° C. More acetone (50 mL) was used to dissolve residual potassium permanganate. The resulting mixture was stirred at −28° C. overnight.

The reaction mixture was filtered through a pad of celite and it was washed with acetone (3×70 mL). The filtrates were concentrated under reduced pressure and the crude material was purified via silica gel flash column chromatography with a 80 g silica cartridge using hexane:ethyl acetate 10-30% as solvent system in order to afford the desired product, 1-(3-methoxybenzyl)-2-(3-((4-(trifluoromethyl)benzyl)sulfonyl)prop-1-en-1-yl)disulfane, as a colourless solid with Z:E 86:14 (753 mg, 51% yield).

Example 4—Minimum Biofilm Inhibition Concentration (MBIC) of 1-(trifluoromethyl)-4-{[(3-{[4-(trifluoromethyl)phenyl]methanesulfonyl}prop-1-en-1-yl)disulfanyl]methyl}benzene The inhibitory activity of the following compound of formula (I) on *Staphylococcus aureus* and *Pseudomonas aeruginosa* was compared to ajoene and DMSO (dimethyl sulphoxide).

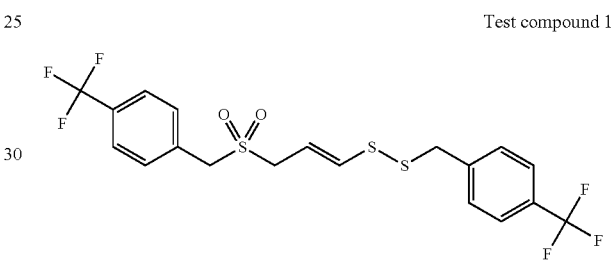

Test compound 1

Compounds were assayed for their ability to inhibit *S. aureus* or *P. aeruginosa* biofilm formation as follows. All compounds were prepared as a 30 mM stock in DMSO and diluted in TSB to 48 μM (*S. aureus*) or 144 μM (*P. aeruginosa*). The compounds were further serially diluted two-fold from 48 μM to 0.75 μM (*S. aureus*) or 144 μM to 2.3 μM (*P. aeruginosa*) and added to a 96-well plate at 100 μl per well. Overnight cultures of bacteria were diluted to an $OD_{600}$=0.07 in fresh TSB and 100 μl of the diluted bacterial culture was added to the compound containing wells. The bacteria were incubated in the presence of the compounds overnight at 37° C. After incubation, the planktonic bacteria were removed by three washes using $H_2O$ and the remaining biofilm was stained using crystal violet and quantified photometrically at $A_{570}$. Absorbances corresponding to biofilm mass were plotted versus compound concentration and $IC_{50}$ values were calculated. Reference: O'Toole GA. Microtiter Dish Biofilm Formation Assay. J. Vis. Exp. (2011).

Figure 2:
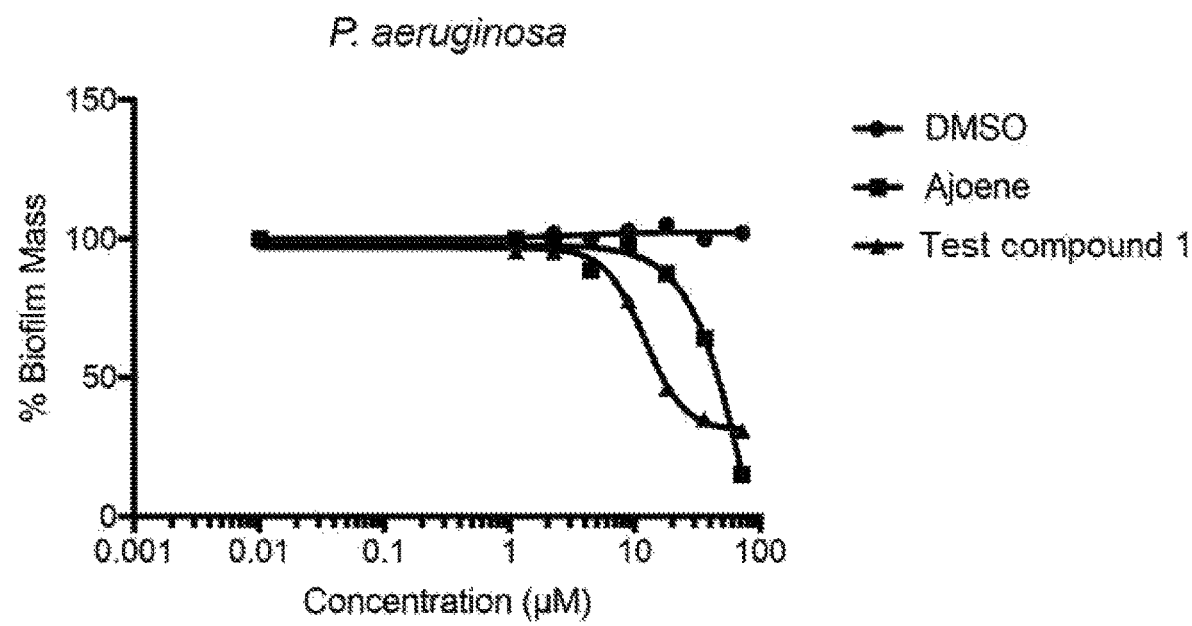
FIG. 2 shows the plot of concentration versus % *P. aeruginosa* biofilm mass for the compound of formula (I) tested in example 4 compared to ajoene and DMSO.

The results are shown in FIGS. 1 and 2. It was surprisingly found that the compound of formula (I) (test compound 1) had a lower 1050 than ajoene against both *Staphylococcus aureus* and *Pseudomonas aeruginosa*.

Example 5—Minimum Biofilm Inhibition Concentration (MBIC) Assay in Reference to Ajoene Control MBIC assays of the compounds are carried out alongside ajoene for reference and standardization. The 1050 of ajoene against *S. aureus* and *P. aeruginosa* is well-defined and reproducible allowing ajoene to serve as an effective control for the experiment. As such, the 1050 calculated for the tested compounds are compared to the 1050 of ajoene in every experiment and are therefore represented as % of ajoene.

If in a given experiment a compound had an 1050 at 100% of ajoene, this compound would be equally as effective as ajoene. If a compound has an 1050<100% of ajoene then this compound is more effective than ajoene. If a compound has an IC50>100% of ajoene then this compound is less effective than ajoene.

Table 1 below shows M BIC results of representative compounds having the structure of Formula (I).

TABLE 1

| Structure | P. aeruginosa MBIC: % of Ajoene positive control IC50 | S. aureus MBIC: % of Ajoene positive control IC50 |
|---|---|---|
| 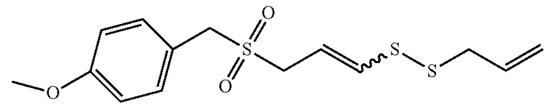 [SMILES: C=CCSSC=CCS(=O)(=O)Cc1ccc(OC)cc1] | 87 | 4 |
| 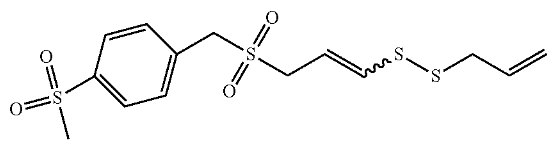 [SMILES: C=CCSSC=CCS(=O)(=O)Cc1ccc(S(C)(=O)=O)cc1] | 82 | 23 |
| 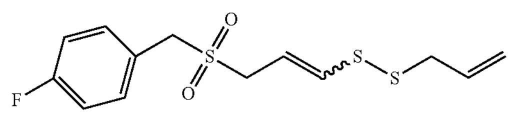 [SMILES: C=CCSSC=CCS(=O)(=O)Cc1ccc(F)cc1] | 49.2 | 7 |
| 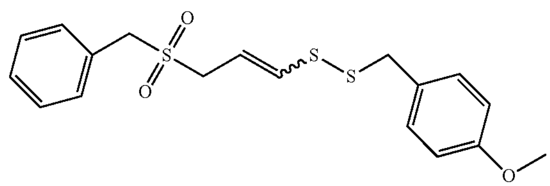 [SMILES: COc1ccc(CSSC=CCS(=O)(=O)Cc2ccccc2)cc1] | 56 | 75 |
| 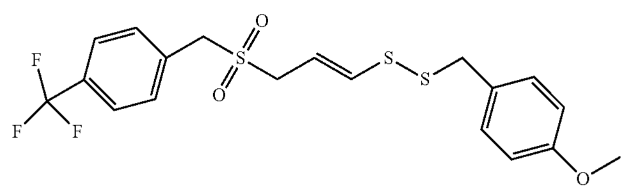 [SMILES: COc1ccc(CSS/C=C/CS(=O)(=O)Cc2ccc(C(F)(F)F)cc2)cc1] | 27.8 | 8.2 |
| 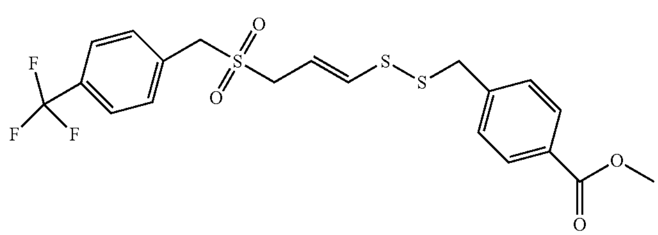 [SMILES: COC(=O)c1ccc(CSS/C=C/CS(=O)(=O)Cc2ccc(C(F)(F)F)cc2)cc1] | 34.7 | 20.5 |
| 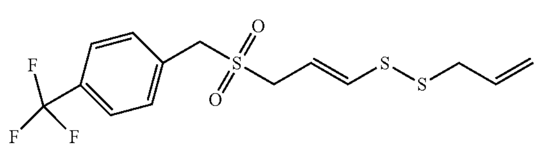 [SMILES: C=CCSS/C=C/CS(=O)(=O)Cc1ccc(C(F)(F)F)cc1] | 78.7 | 55.5 |
| 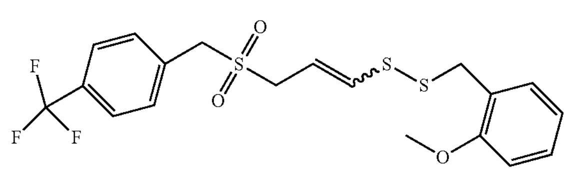 [SMILES: COc1ccccc1CSSC=CCS(=O)(=O)Cc1ccc(C(F)(F)F)cc1] | 13.9 | 51 |

TABLE 1-continued

| Structure | P. aeruginosa MBIC: % of Ajoene positive control IC50 | S. aureus MBIC: % of Ajoene positive control IC50 |
|---|---|---|
| 4-CF₃-C₆H₄-CH₂-SO₂-CH=CH-CH₂-S-S-CH₂-C₆H₄-3-OCH₃ | 65.3 | 20 |
| 4-CF₃-C₆H₄-CH₂-SO₂-CH=CH-CH₂-S-S-CH₂-C₆H₄-4-OCH₃ | 79 | 24 |
| 4-CF₃-C₆H₄-CH₂-SO₂-CH=CH-CH₂-S-S-CH₂-C₆H₄-4-CF₃ | 45.3 | 28.6 |
| 4-CF₃-C₆H₄-CH₂-SO₂-CH=CH-CH₂-S-S-CH₂-CH=CH₂ | 42.75 | 38.6 |
| cyclopropyl-CH₂-SO₂-CH=CH-CH₂-S-S-CH₂-cyclopropyl | 57.5 | 69.18 |
| 2-furyl-CH₂-SO₂-CH=CH-CH₂-S-S-CH₂-CH=CH₂ | 11.7 | 21.9 |
| 2-thienyl-CH₂-SO₂-CH=CH-CH₂-S-S-CH₂-CH=CH₂ | 29.7 | 52 |

Example 6—Comparison of Inhibitory Activity of 1-{[-3-(prop-2-en-1-yldisulfanyl)prop-2-ene-1-sulfonyl]methyl}-4-(trifluoromethyl)benzene with Other Biofilm Inhibitory Agents The inhibitory activity of the following compound on *Staphylococcus aureus* and *Pseudomonas aeruginosa* was compared to other biofilm inhibitory agents, i.e. ajoene, cysteamine, gallium nitrate, HDMF, and C-30.

Test compound 2

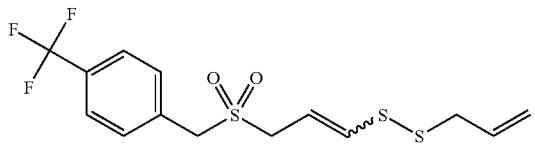

The structures of HDMF, cysteamine, gallium nitrate, and C-30 are shown below.

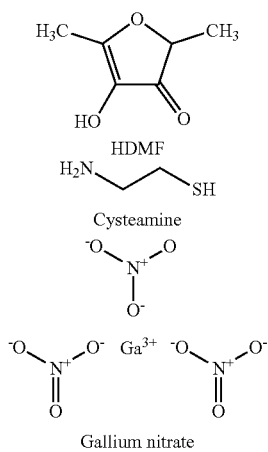

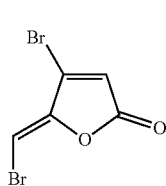

The compound and the other biofilm inhibitory agents were assayed for their inhibitory activity using the MBIC method as described in Example 4. Absorbances corresponding to biofilm mass were plotted versus concentration of compound and other biofilm inhibitory agents.

Figure 3:
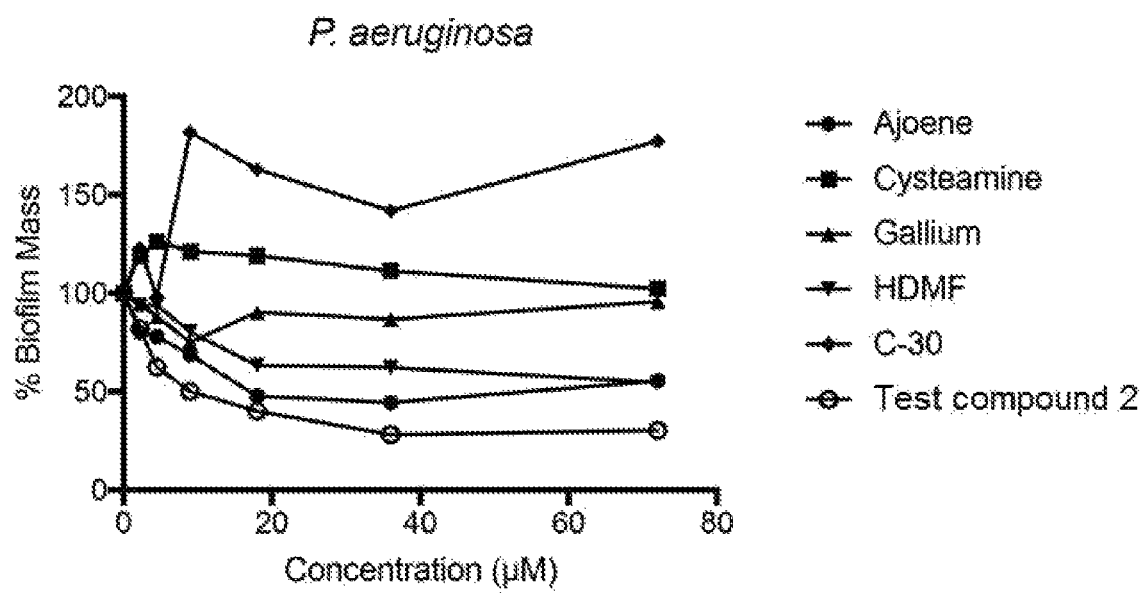
FIG. 3 shows the plot of concentration versus % *P. aeruginosa* biofilm mass for the compound of formula (I) tested in example 6 compared to ajoene, HDMF, cysteamine, gallium nitrate, and C-30.
Figure 4:
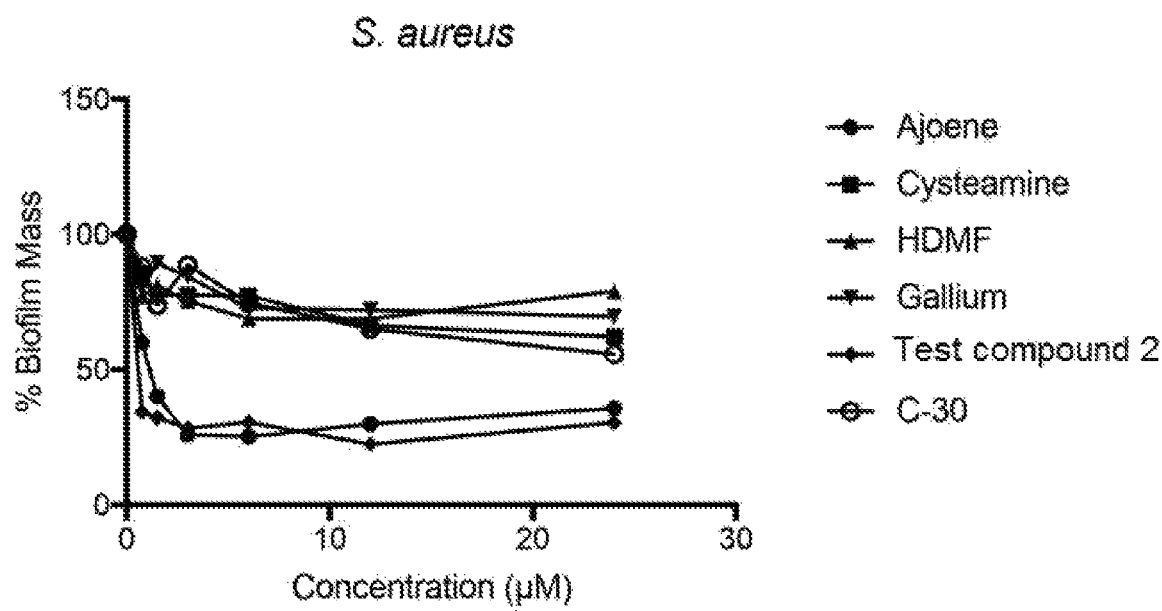
FIG. 4 shows the plot of concentration versus % *S. aureus* biofilm mass for the compound of formula (I) tested in example 6 compared to ajoene, HDMF, cysteamine, gallium nitrate, and C-30.

The results are shown in FIGS. 3 and 4. It was surprisingly found that the compound of formula (I) (test compound 2) had an improved inhibitory activity compared to ajoene, cysteamine, gallium nitrate, HDMF, and C-30.

Example 7—Scratch Closure Test

HaCaT cells (aneuploidy immortal keratinocyte cell line) were seeded in a 96-well plate at a cell density of $5 \times 10^4$ cells per well and incubated overnight at 37° C., 5% $CO_2$ and 95% humidity. Test and control compounds were prepared in 1% DMSO and diluted to a concentration of 5 μM in pre-warmed HaCaT cell media. Cells were washed with pre-warmed PBS and the monolayers mechanically injured by introducing a vertical cell-free area in each individual well, and washed again. Test and control compounds were added and all wells microscopically imaged for time point 0. Cells were incubated as described above and imaged after 20 hours. All conditions were tested with an N of 4 replicates.

Scratch closure was analysed using ImageJ software and standard deviation calculated. Scratch closure area reduction was plotted using GraphPrism 8 software.

The compound of formula (I) that was tested had the following structure:

Test compound 3

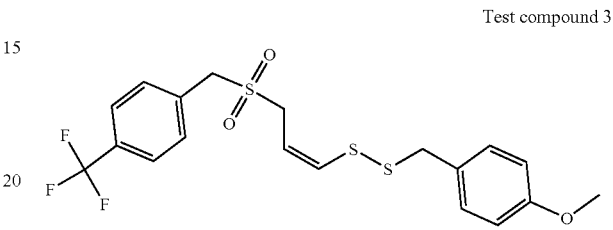

The comparative compounds were E-ajoene, sulforaphane (SFN), 1% DMSO (vehicle control), epithelial growth factor (EGF) (positive control (pos)), and BAY 61-3606 hydrochloride hydrate (negative control (neg)).

Figure 5:
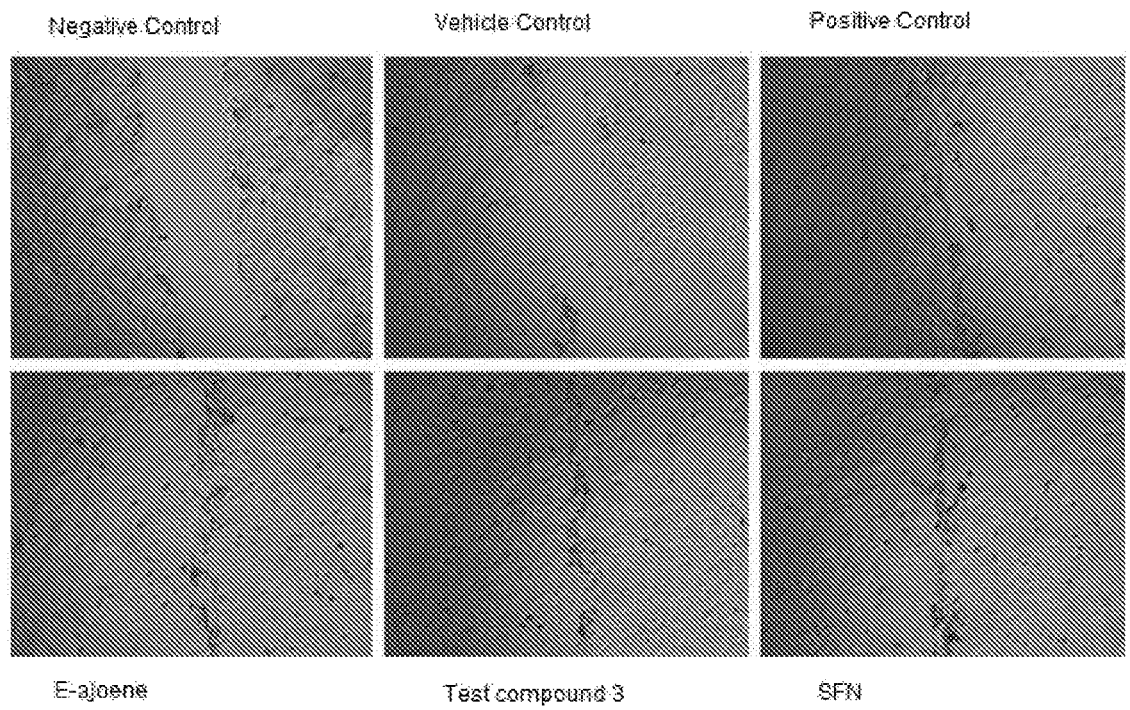
FIG. 5 shows microscopic images of the samples of the scratch test described in example 7.
Figure 6:
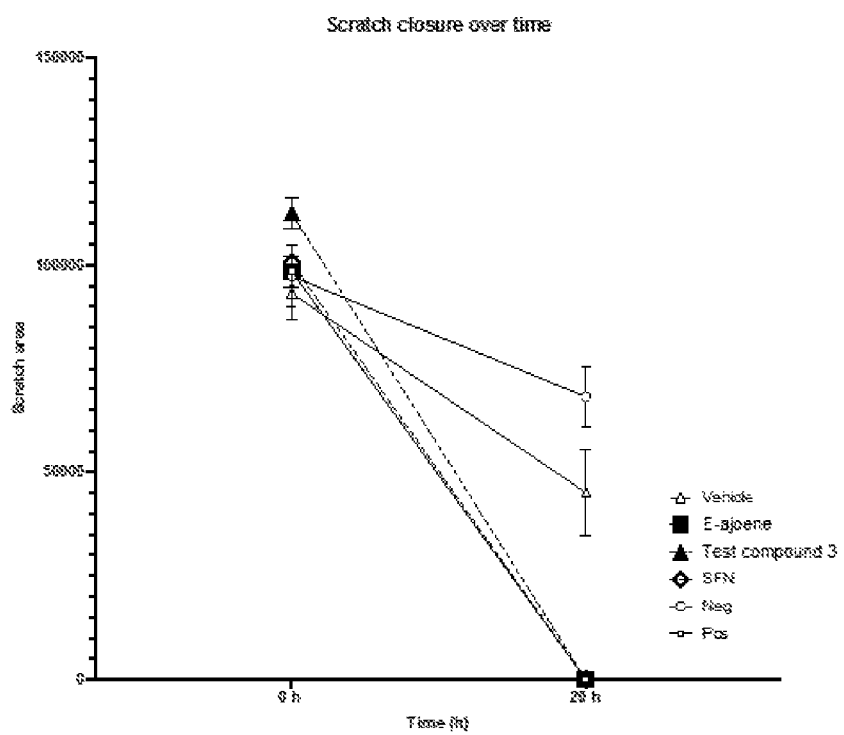
FIG. 6 shows the plot of time (h) versus scratch area for the compounds of formula (I) tested in example 7 compared to vehicle control, sulforaphane, EGF positive control and BAY 61-3606 hydrochloride hydrate negative control.

The results are shown in FIGS. 5 and 6.

Test compound 3, E-ajoene and sulforaphane at 5 μM all show enhanced scratch closure compared to vehicle control (P<0.0001), with complete scratch closure observed at 20 h in line with an epithelial growth factor (EGF) positive control.

The foregoing broadly describes certain embodiments of the present invention without limitation. Variations and modifications as will be readily apparent to those skilled in the art are intended to be within the scope of the present invention as defined in and by the appended claims.

The invention claimed is:

1. A compound of formula (I)

Formula (I)

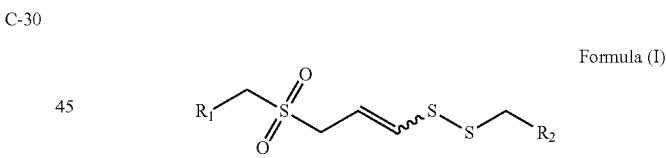

wherein;

$R_1$ is phenyl, substituted phenyl, cycloalkyl, substituted cycloalkyl, hetercyclyl, or substituted heterocyclyl; and $R_2$ is phenyl, substituted phenyl, cycloalkyl, substituted cycloalkyl, or alkenyl.

2. The compound of claim 1, wherein $R_1$ is the substituted phenyl, and the substituted phenyl is alkylphenyl, haloalkylphenyl, alkylbenzoate, alkoxyphenyl, halophenyl, alkylphenyl sulphone, haloalkoxyphenyl, or aminophenyl.

3. The compound of claim 2, wherein the haloalkylphenyl is halomethylphenyl or trifluoromethylphenyl.

4. The compound of claim 2, wherein the alkylbenzoate is methylbenzoate.

5. The compound of claim 2, wherein the alkoxyphenyl is methoxyphenyl.

6. The compound of claim 2, wherein the halophenyl is fluorophenyl.

7. The compound of claim 2, wherein the alkylphenyl sulphone is methylphenyl sulphone.

8. The compound of claim 2, wherein the haloalkoxyphenyl is fluoromethoxyphenyl.

9. The compound of claim 2, wherein the aminophenyl is dimethylaminophenyl.

10. The compound of claim 1, wherein $R_2$ is the substituted phenyl, and the substituted phenyl is haloalkylphenyl, alkylbenzoate or alkoxyphenyl.

11. The compound of claim 1, wherein the cycloalkyl is cyclopropyl.

12. The compound of claim 1, wherein the alkenyl is ethenyl.

13. The compound of claim 1, wherein the heterocyclyl is a heteroaryl and/or wherein the substituted heterocyclyl is a substituted heteroaryl.

14. The compound of claim 1, wherein the heterocyclyl is furan or thiophene and/or wherein the substituted heterocyclyl is substituted furan or substituted thiophene.

15. The compound of claim 1, wherein the compound is:

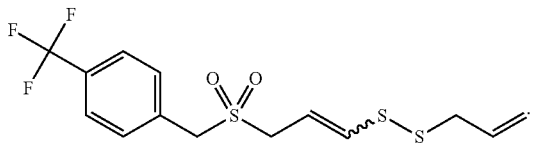

16. A pharmaceutical composition comprising a compound of claim 1 and a pharmaceutically acceptable excipient and/or carrier and/or diluent.

17. A method for treating a microbial infection and/or for treating inflammation and/or for reducing the formation of blood clots, wherein the method comprises administering a compound of claim 1 to a subject.

18. The compound of claim 1, wherein the compound is

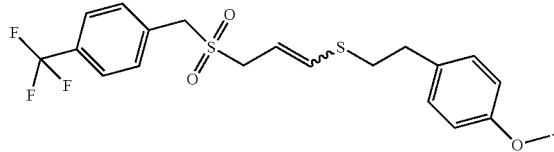

19. A method for treating a wound, wherein the method comprises administering a compound of claim 1 to a subject.

20. A method for treating epidermolysis bullosa, wherein the method comprises administering a compound of claim 1 to a subject.

* * * * *